United States Patent [19]
Hancock et al.

[11] Patent Number: 6,057,291
[45] Date of Patent: *May 2, 2000

[54] ANTIMICROBIAL CATIONIC PEPTIDES

[75] Inventors: Robert E. W. Hancock, Vancouver, Canada; Nedra Karunaratne, Kandy, Sri Lanka

[73] Assignee: University of British Columbia, Vancouver, Canada

[*] Notice: This patent is subject to a terminal disclaimer.

[21] Appl. No.: 08/763,226

[22] Filed: Dec. 10, 1996

Related U.S. Application Data

[63] Continuation-in-part of application No. 08/658,857, May 31, 1996, which is a continuation-in-part of application No. 08/460,464, Jun. 2, 1995, Pat. No. 5,877,274.

[51] Int. Cl.$^7$ ................................................. A61K 38/00
[52] U.S. Cl. .............................. 514/12; 514/13; 530/324; 530/326
[58] Field of Search ....................... 514/12, 13; 530/324, 530/326

[56] References Cited

U.S. PATENT DOCUMENTS 5,585,353  12/1996  Merrifield et al. ..................... 514/12
5,593,866   1/1997  Hancock et al. ..................... 435/69.7

FOREIGN PATENT DOCUMENTS

WO9628559-A1  9/1996  WIPO.
WO 96/38473  12/1996  WIPO.

OTHER PUBLICATIONS

Bowman et al. (1996) GenBank Accession No. W23487.
Brown et al. (1997) GenBank Accession No. W14735.
Brown et al. (1996) GenBank Accession No. W00275.

*Primary Examiner*—Rebecca E. Prouty
*Assistant Examiner*—Enrique D. Longton
*Attorney, Agent, or Firm*—Fish & Richardson P. C.

[57] ABSTRACT

A novel class of cationic peptides having antimicrobial activity is provided. Examples of such peptides include $NH_2$—KWKSFIKKLTTAVKKVLTTGLPALIS—COOH (SEQ ID NO:1) and $NH_2$—KWKSFIKKLTSAAKKVVTTAKPLISS—COOH (SEQ ID NO:2). Also provided are methods for inhibiting the growth of bacteria utilizing the peptides of the invention. The peptides are particularly useful for inhibiting endotoxemia in a subject.

10 Claims, 12 Drawing Sheets

CEME

MBI — 29

MBI — 26

ANTIMICROBIAL CATIONIC PEPTIDES

This application is a continuation-in-part application of U.S. patent application Ser. No. 08/658,857 filed May 31, 1996, which is a continuation-in-part application of U.S. patent application Ser. No. 08/460,464 filed on Jun. 2, 1995 now U.S. Pat. No. 5,877,274.

BACKGROUND OF THE INVENTION

1. Field of the Invention

This invention relates generally to antimicrobial peptides and specifically to a new class of antimicrobial cationic peptides referred to as bactolysins.

2. Description of Related Art

In 1981, the self-promoted uptake hypothesis was first proposed to explain the mechanism of action of polycationic antibiotics in *Pseudomonas aeruginosa*. According to this hypothesis, polycations interact with sites on the outer membranes of Gram-negative bacteria at which divalent cations cross-bridge adjacent lipopolysaccharide molecules. Due to their higher affinity for these sites, polycations displace the divalent cations and, since the polycations are bulkier than the divalent cations, cause structural perturbations in the outer membrane. These perturbations result in increased outer membrane permeability to compounds such as the β-lactam antibiotic nitrocefin, the eukaryotic non-specific defense protein lysozyme and to hydrophobic substances. By analogy, molecules accessing this pathway are proposed to promote their own uptake.

It has been clearly demonstrated that the outer membranes of Gram-negative bacteria are semipermeable molecular "sieves" which restrict access of antibiotics and host defense molecules to their targets within the bacterial cell. Thus, cations and polycations which access the self-promoted uptake system are, by virtue of their ability to interact with and break down the outer membrane permeability barrier, capable of increasing the susceptibility of Gram-negative pathogenic bacteria to antibiotics and host defense molecules. Hancock and Wong demonstrated that a broad range of such compounds could overcome the permeability barrier and coined the name "permeabilizers" to describe them (Hancock and Wong, *Antimicrob. Agents Chemother.*, 26:48, 1984). While self-promoted uptake and permeabilizers were first described for *P. aeruginosa*, they have now been described for a variety of Gram-negative bacteria.

Over the past decade, non-specific defense molecules have been described in many animals, including insects and humans. One subset of these molecules have in common the following features: (a) they are small peptides, usually 15–35 amino acids in length, (b) they contain 4 or more positively charged amino acid residues, either lysines or arginines, and (c) they are found in high abundance in the organisms from which they derive. Several of these molecules have been isolated, amino acid sequenced and described in the patent literature (e.g., cecropins: WO8900199, WO 8805826, WO8604356, WO 8805826; defensins: EP 193351, EP 85250, EP 162161, U.S. Pat. No. 4,659,692, WO 8911291). However, only limited amounts of these peptides can be isolated from the host species. For example, Sawyer, et al., (*Infect. Immun.* 56:693, 1988) isolated 100–200 mg of rabbit neutrophil defensins 1 and 2 from $10^9$ primed peritoneal neutrophils or lipopolysaccharide-elicited alveolar macrophages (i.e., the numbers present in a whole animal).

The gene for human defensin has been cloned and sequenced, but no successful expression has been demonstrated, as yet. Furthermore, production of these peptides using peptide synthesis technology produces peptides in limited amounts and is expensive when scaled up or when many variant peptides must be produced. Also, structural analysis is difficult without specific incorporation of $^{15}N$ and $^{13}C$ tagged amino acids which is prohibitively expensive using amino acid synthesis technology.

There is a need to develop polypeptides having a broad range of potent antimicrobial activity against a plurality of microorganisms, including gram negative bacteria, gram positive bacteria, fungi, protozoa, viruses and the like.

SUMMARY OF THE INVENTION

The present invention provides a novel class of cationic peptides, referred to as bactolysins, which have antimicrobial activity. Two representative peptides are provided and include MBI29, $NH_2$—KWKSFIKKLTTAVKKVLTTGLPALIS—COOH (SEQ ID NO:1) and MBI26, $NH_2$—KWKSFIKKLTSAAKKVVTTAKPLISS—COOH (SEQ ID NO:2), analogs, derivatives and conservative variations thereof.

The invention also provides a method of inhibiting the growth of bacteria comprising contacting the bacteria with an inhibiting effective amount of a peptide having an amino acid sequence of MBI 29 (SEQ ID NO:1) or MBI 26 (SEQ ID NO:2) alone, or in combination with an antibiotic. Classes of antibiotics which can be used for synergistic therapy with the peptides of the invention include aminoglycoside, penicillin, cephalosporine, fluoroquinolone, carbepenem, tetracycline and macrolide.

In another embodiment, the invention provides a method of inhibiting an endotoxemia or sepsis associated disorder in a subject having or at risk of having such a disorder, comprising administering to the subject a therapeutically effective amount of a peptide of the invention.

DETAILED DESCRIPTION OF THE INVENTION

Figures 1A, 1B, 1C:
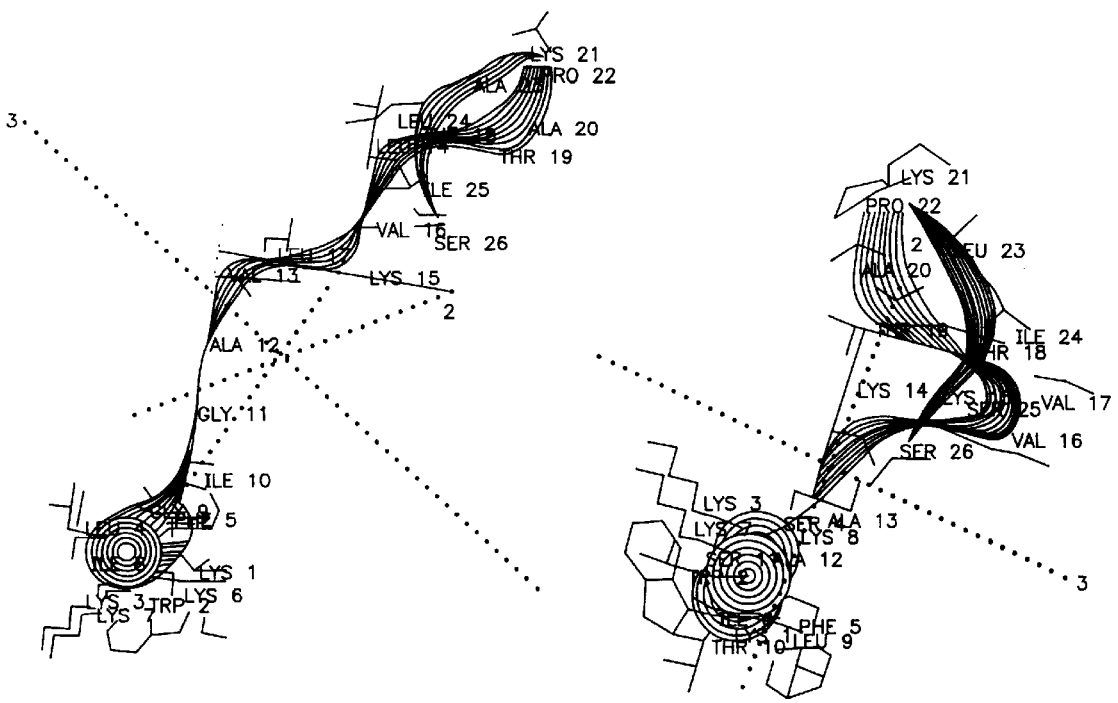
FIG. 1 shows a three-dimensional schematic representation of the conformational structure of CEME, MBI 29, and MBI 26.

The present invention provides a novel classs of cationic peptides, called bactolysins, which have antimicrobial activity and have the ability to significantly reduce the level of lipopolysaccharide (LPS)-induced tumor necrosis factor (TNF). These peptides are useful for inhibiting microbial infection or growth, as well reducing the effects of endotoxemia and are often synergistic with conventional antibiotics and/or lysozyme. In addition, such peptides are useful as antifungal agents, antitumor agents, or antiviral agents.

The term "antimicrobial" as used herein means that the peptides of the present invention inhibit, prevent, or destroy the growth or proliferation of microbes such as bacteria, fungi, viruses or the like. The term "antiviral" as used herein means that the peptides of the present invention inhibit, prevent or destrroy the growth or proliferation of viruses or of virally-infected cells. The term "anti-tumor" as used herein means that the peptides of the present invention may be used to inhibit the growth of or destroy tumors. The term "antifungal" as used herein means that the peptides of the present invention may be used to inhibit the growth of or destroy fungi.

In a first embodiment, the invention provides an isolated antimicrobial peptide having an amino acid sequence:
NH$_2$—KWKR$_2$R$_1$R$_1$R$_2$R$_2$R$_1$R$_2$R$_2$R$_1$R$_1$R$_2$R$_2$VLTTGLPALIS—COOH (SEQ ID NO:26),
NH$_2$—KWKR$_2$R$_1$R$_1$R$_2$R$_2$R$_1$R$_2$R$_2$R$_1$R$_1$R$_2$R$_2$VVTTAKPLISS—COOH (SEQ ID NO:27),
NH$_2$—KWKR$_2$R$_1$R$_1$R$_2$R$_2$R$_1$R$_2$R$_2$R$_1$R$_1$R$_2$R$_2$ILTTGLPALIS—COOH (SEQ ID NO:28),
NH$_2$—KWKR$_2$R$_1$R$_1$R$_2$R$_2$R$_1$R$_2$R$_2$R$_1$R$_1$R$_2$R$_2$GGLLSNIVTSL—COOH (SEQ ID NO:29),
or NH$_2$—KWKR$_2$R$_1$R$_1$R$_2$R$_2$R$_1$R$_2$R$_2$R$_1$R$_1$R$_2$R$_2$GPILANLVSIV—COOH (SEQ ID NO:30)
wherein R$_1$ is a hydrophobic amino acid residue and $_2$R is a hydrophilic amino acid residue.

Examples of such peptides of the invention include but are not limited to:
NH$_2$—KWKSFIKKLTTAVKKVLTTGLPALIS—COOH (MBI 29) (SEQ ID NO:1),
NH$_2$—KWKSFIKKLTSAAKKVVTTAKPLISS—COOH (MBI 26) (SEQ ID NO:2),
NH$_2$—KWKSFIKNLTKGGSKILTTGLPALIS—COOH (MBI 201) (SEQ ID NO:3),
NH$_2$—KWKKFIKNLTKGGSKILTTGLPALIS—COOH (MBI 202) (SEQ ID NO:4),
NH$_2$—KWKSFIKNLEKVLKPGGLLSNIVTSL—COOH (MBI 490) (SEQ ID NO:5),
NH$_2$—KWKSFIKNLEKVLKKGPILANLVSIV—COOH (MBI 491) (SEQ ID NO:6),
NH$_2$—KWKEFIKKLTTAVKKVLTTGLPALIS—COOH (MBI 492) (SEQ ID NO:7),
NH$_2$—KWKKFIKELQKVLAPGGLLSNIVTSL—COOH (MBI 493) (SEQ ID NO:8),
NH$_2$—KWKSFIKKLTSVLKKVVTTALPALIS—COOH (MBI 29A1) (SEQ ID NO:9),
NH$_2$—KWKSFIKNLTKVLKKVVTTALPALIS—COOH (MBI 29A2) (SEQ ID NO:10),
NH$_2$—KWKLFKKKGTGAVLTVLTTGLPALIS—COOH (MBI 29A3) (SEQ ID NO:11),
NH$_2$—KWKSFIKKLTSVLKKVVTTAKPLISS—COOH (SEQ ID NO: 12),
NH$_2$—KKKSFIKLLTSAKVSVLTTAKPLISS—COOH (SEQ ID NO:13), and
NH$_2$—KWKKFIKELQKVLKPGGLLSNIVTSL—COOH (SEQ ID NO:14), analogs, derivatives and conservative variations thereof, wherein the peptides have antimicrobial activity. The peptides of the invention include SEQ ID NO:1–14, as well as the broader groups of peptides having hydrophilic and hydrophobic substitutions, and conservative variations thereof.

The sequence KWKSFIKK (SEQ ID NO:34), as found in the first 8 NH$_2$ terminal amino acids of peptides in SEQ ID NO:1 and 2, is important for conferring antimicrobial activity. The presence of a positively charged amino acid (lysine or arginine) at positions 11, 14, 15 and 21 are also very important in antimicrobial activity. A further enhancement of antimicrobial activity can be achieved by making conservative changes in the residues designated R$_1$ and R$_2$.

In another embodiment, the invention provides an isolated antimicrobial peptide having an amino acid sequence:
NH$_2$—KKWWRRR$_1$R$_1$R$_2$R$_1$R$_1$R$_2$R$_2$GPALSNV—COOH (SEQ ID NO:31)
wherein R$_1$ is a hydrophobic amino acid residue and $_2$R is a hydrophilic amino acid residue. Examples of such peptides of the invention include but are not limited to:
NH$_2$—KKWWRRVLSGLKTGPALSNV—COOH (SEQ ID NO:15),
NH$_2$—KKWWRRVLKGLSSGPALSNV—COOH (SEQ ID NO:16), and
NH$_2$—KKWWRRALQALKNGPALSNV—COOH (SEQ ID NO:17), analogs, derivatives and conservative variations thereof, wherein the peptides have antimicrobial activity. The peptides of the invention include SEQ ID NO: 15–17, as well as the broader groups of peptides having hydrophilic and hydrophobic substitutions, and conservative variations thereof.

In another embodiment, the invention provides an isolated antimicrobial peptide having an amino terminal amino acid sequence:
NH$_2$—KKWWRRX (SEQ ID NO:32). Preferably, the peptide is from about 20 to about 30 amino acids in length and therefore X is from about 14 to about 24 amino acids. Most preferably the peptide has a sequence of
NH$_2$—KKWWRRR$_1$R$_1$R$_2$GLKTAGPAIQSVLNK—COOH (SEQ ID NO:35)
wherein R$_1$ is a hydrophobic amino acid residue and R$_2$ is a hydrophilic amino acid residue. Examples of such peptides of the invention include but are not limited to:
NH$_2$—KKWWRRVLSGLKTAGPAIQSVLNK—COOH (MBI 21A1) (SEQ ID NO:18), and
NH$_2$—KKWWRRALQGLKTAGPAIQSVLNK—COOH (MBI 21A2) (SEQ ID NO:19), analogs, derivatives and conservative variations thereof, wherein the peptides have antimicrobial activity. The peptides of the invention include SEQ ID NO:18–19, as well as the broader groups of peptides having hydrophilic and hydrophobic substitutions, and conservative variations thereof.

In another embodiment, the invention provides an isolated antimicrobial peptide having an amino terminal amino acid sequence:
NH$_2$—KKWWKX (SEQ ID NO:33). Preferably, the peptide is from about 20 to about 30 amino acids in length and therefore X is from about 14 to about 24 amino acids. Most preferably the peptide has a sequence of NH$_2$—KKWWKAQKAVNSGPNALQTLAQ—COOH (SEQ ID NO:20)
NH$_2$—KKWWKAKKFANSGPNALQTLAQ—COOH (SEQ ID NO:21), or
NH$_2$—KKWWKFIKKAVNSGTTGLQTLAS—COOH (SEQ ID NO:22), analogs, derivatives and conservative variations thereof, wherein the peptides have antimicrobial activity. The peptides of the invention include SEQ ID NO:20–22, as well as the broader groups of peptides having hydrophilic and hydrophobic substitutions, and conservative variations thereof.

Other cationic peptides of the invention include:
NH$_2$—KKSFFKKLTSVASSVLS—COOH (MBI 21A14) (SEQ ID NO:23),
NH$_2$—WKVFKSFIKKASSFAQSVLD—COOH (SEQ ID NO:24), and
NH$_2$—KKWRKSFFKQVGSFDNSV—COOH (SEQ ID NO:25), analogs, derivatives and conservative variations thereof, wherein the peptides have antimicrobial activity.

Figure 2A:
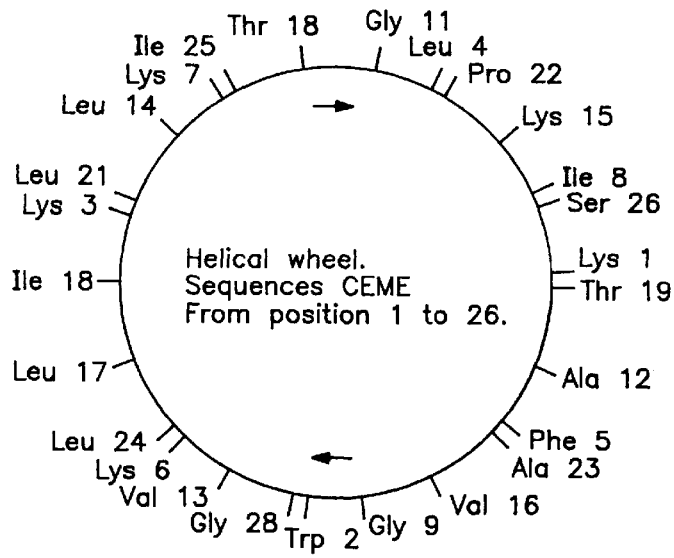
FIG. 2 shows the axial projection of the α-helical conformation of each peptide in 2D.
Figure 2B:
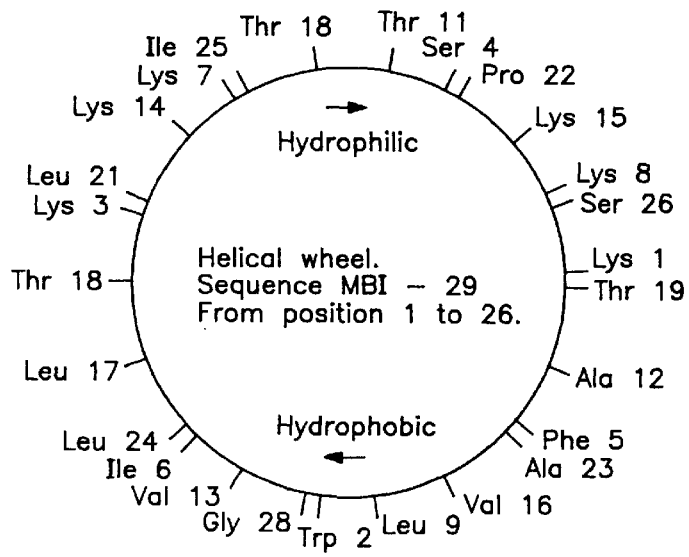
Figure 2C:
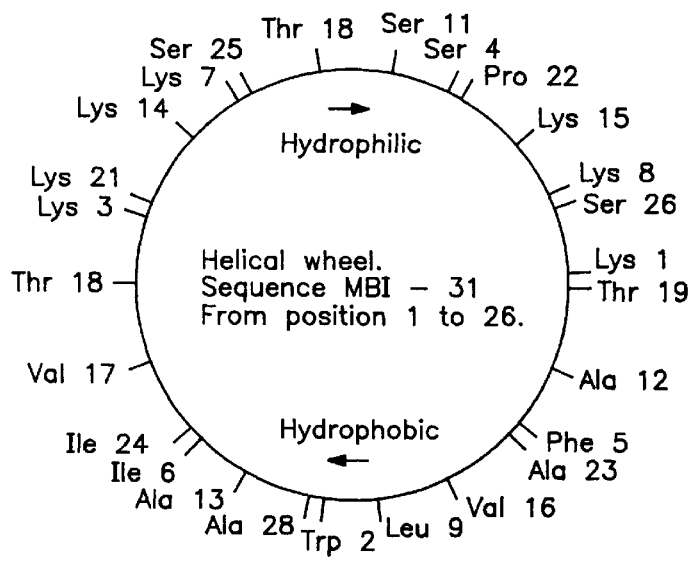

The sequence of SEQ ID NO:1 contains helix-forming hydrophilic amino acids at residues 4, 8, 10, 11, and 14. Amino acids 6 and 9 are hydrophobic residues (see FIG. 1). The helical nature of the first 10 amino acids is depicted in FIGS. 1 and 2. The cationic charge of the peptide of SEQ ID NO:1 was achieved by placing a lysine at positions 8 and 14, thereby increasing the total positive charge to 6. The carboxy terminus of SEQ ID NO: 1 was converted to the methyl ester and the antibacterial activity of this derivative was the same as that of the unmodified peptide. The peptide of SEQ ID NO: 1 also has antifungal activity. Amino acid residues 3, 4, 7, 8, 10, 11, 14, and 15 are preferably hydrophilic residues, while amino acid residues 2, 5, 6, 9, 12, and 13 are preferably hydrophobic residues.

SEQ ID NO: 1 was modified to increase the alpha helical nature by changing amino acids in the C-terminal tail, thereby resulting in SEQ ID NO:2. Amino acids 11 (neutral hydrophilic) and 13 (hydrophobic) of SEQ ID NO: 1 were changed to another neutral hydrophilic and hydrophobic amino acid, respectively, in order to increase alpha helicity in this region. The C-terminal tail (residue 20–26) was modified to include a positive charge and increase alpha helicity. Therefore residues 20, 21, 23, 24 and 25 were changed (See FIGS. 1 and 2). SEQ ID NO:3 was obtained by changing amino acids 8, 1 1, 12, 13, 14, and 16 of SEQ ID NO:1. The first 15 amino acid residues contain lysine at every fourth residue of the alpha helix. Thus, the lysines at positions 8 and 14 in SEQ ID NO: 1 were replaced by asparagine and serine, respectively, and the serine at position 11 was c-hanged to lysine. Further changes were made at positions 12, 13 and 16 to conserve the helical nature. The C-terminal tail was unchanged SEQ ID NO:4 is identical to SEQ ID NO:3, except for the amino acid at position 4, which incorporates an additional positive charge. SEQ ID NO:5 and SEQ ID NO:6 represent peptides having the same amino acid sequence as SEQ ID NO:3 for the first 9 amino acids. The amino acid at position 10 is glutamic acid. Residues 10, 11, 12, and 13 in both SEQ ID NO:5 and SEQ ID NO:6 are different than SEQ ID NO:1, but remain either hydrophilic or hydrophobic as described above.

Residue 14 in SEQ ID NO:5 is the same as in SEQ ID NO:1. All residues thereafter, 15-26, are completely changed to construct a hydrophobic helical tail, and bears no resemblance to the tail of SEQ ID NO: 1. SEQ ID NO:6 contains the same residues as SEQ ID NO:1 at positions 14 and 15. Residues 16–26 have been changed to form a helical tail.

The term "isolated" as used herein refers to a peptide substantially free of proteins, lipids, nucleic acids, for example, with which it is naturally associated. Those of skill in the art can make similar substitutions to achieve peptides with greater antibacterial activity and a broader host range. For example, the invention includes the bactolysin peptides depicted in SEQ ID NO: 1–25, as well as analogues or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists.

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, so long as the bioactivity as described herein is remains. All peptides were synthesized using L amino acids, however, all D forms of the peptides (e.g., see Table 1b, CEMA) can be synthetically produced. In addition, C-terminal derivatives can be produced, such as C-terminal methyl esters, in order to increase the antimicrobial activity of a peptide of the invention.

The peptide of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substitued for one another include asparagine, glutamine, serine and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention with respect to $R_1$ and $R_2$. For the peptides of the invention, a preferred conservative variation is substitution of lysine by arginine.

The biological activity of the peptides can be determined by standard methods known to those of skill in the art, such as "minimal inhibitory concentration (MIC)" assay described in the present examples, whereby the lowest concentration at which no change in OD is observed for a given period of time is recorded as MIC. Alternatively, "fractional inhibitory concentration (FIC)" is also useful for determination of synergy between the peptides of the invention, or the peptides in combination with known antibiotics. FICs are performed by checkerboard titrations of peptides in one dimension of a microtiter plate, and of antibiotics in the other dimension, for example. The FIC is calculated by looking at the impact of one antibiotic on the MIC of the other and vice versa An FIC of one indicates that the influence of the compounds is additive and an FIC of less than one indicates synergy. Preferably, an FIC of less than 0.5 is obtained for synergism. As used herein, FIC can be determined as follows:

FIC=MIC (peptide in combination)+
 MIC (antibiotic in combination)
 MIC (peptide alone) MIC (antibiotic alone)

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention includes polynucleotides encoding:

$NH_2$—KWKR$_2$R$_1$R$_1$R$_2$R$_2$R$_1$R$_2$R$_2$R$_1$R$_1$R$_2$R$_2$VLTTGLPALIS—COOH (SEQ ID NO:26), $NH_2$—KWKR$_2$R$_1$R$_1$R$_2$R$_2$R$_1$R$_2$R$_2$R$_1$R$_1$R$_2$R$_2$VVTTAKPLISS—COOH (SEQ ID NO:27), $NH_2$—KWKR$_2$R$_1$R$_1$R$_2$R$_2$R$_1$R$_2$R$_2$R$_1$R$_1$R$_2$R$_2$ILTTGLPALIS—COOH (SEQ ID NO:28), $NH_2$—KWKR$_2$R$_1$R$_1$R$_2$R$_2$R$_1$R$_2$R$_2$R$_1$R$_1$R$_2$R$_2$GGLLSNIVTSL—COOH (SEQ ID NO:29), and $NH_2$—KWKR$_2$R$_1$R$_1$R$_2$R$_2$R$_1$R$_2$R$_2$R$_1$R$_1$R$_2$R$_2$GPILANLVSIV—COOH (SEQ ID NO:30) wherein $R_1$ is a hydrophobic amino acid residue and $R_2$ is a hydrophilic amino acid residue. More specifically, the invention also includes an isolated polynucleotide which encodes the MBI 29 peptide of SEQ ID NO:1, an isolated polynucleotide which encodes the MBI 26 peptide of SEQ ID NO:2, and isolated polynucleotides which encode SEQ ID NO: 3–25. In addition, the invention includes polynucleotides which encode analogs, mutants and variants of the peptides of the invention. The term "isolated" as used herein refers to a polynucleotide substantially free of proteins, lipids, nucleic acids, for example, with which it is naturally associated. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest, such as the peptide of SEQ ID NO: 1–25.

In the present invention, the polynucleotides encoding the cationic peptides of the invention may be inserted into a recombinant "expression vector". The term "expression vector" refers to a plasmid, virus or other vehicle known in the art that has been manipulated by insertion or incorporation of cationic genetic sequences. Such expression vectors of the invention are preferably plasmids which contain a promoter sequence which facilitates the efficient transcription of the inserted genetic sequence in the host. The expression vector typically contains an origin of replication,. a promoter, as well as specific genes which allow phenotypic selection of the transformed cells. For example, the expression of the peptides of the invention can be placed under control of *E. coli* chromosomal DNA comprising a lactose or lac operon which mediates lactose utilzation by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene.

Transformation of a host cell with the polynucleotide may be carried out by conventional techniques well known to those skilled in the art. For example, where the host is prokaryotic, such as *E. coli*, competent cells which are capable of DNA uptake can be prepared from cells harvested after exponential growth and subsequently treated by the CaCl$_2$ method using procedures well known in the art. Alternatively, MgC$_2$l or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art.

DNA sequences encoding the cationic peptides can be expressed in vivo by DNA transfer into a suitable host cell. "Host cells" of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include *E. coli, S. aureus* and *P. aeruginosa*, although other Gram-negative and Gram-positive organisms known in the art can be utilized as long as the expression vectors contain an origin of replication to permit expression in the host.

The cationic peptide polynucleotide sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of mRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., Nuc. Acid Res., 11:2325, 1983).

The invention also provides a method of inhibiting the growth of bacteria comprising contacting the bacteria with an inhibiting effective amount of a peptide of the invention, including:

$NH_2$—KWKR$_2$R$_1$R$_1$R$_2$R$_2$R$_1$R$_2$R$_2$R$_1$R$_1$R$_2$R$_2$VLTTGLPALIS—COOH (SEQ ID NO:26),
$NH_2$—KWKR$_2$R$_1$R$_1$R$_2$R$_2$R$_1$R$_2$R$_2$R$_1$R$_1$R$_2$R$_2$VVTTAKPLISS—COOH (SEQ ID NO:27),
$NH_2$—KWKR$_2$R$_1$R$_1$R$_2$R$_2$R$_1$R$_2$R$_2$R$_1$R$_1$R$_2$R$_2$ILTTGLPALIS—COOH (SEQ ID NO:28),
$NH_2$—KWKR$_2$R$_1$R$_1$R$_2$R$_2$R$_1$R$_2$R$_2$R$_1$R$_1$R$_2$R$_2$GGLLSNIVTSL—COOH (SEQ ID NO:29),
$NH_2$—KWKR$_2$R$_1$R$_1$R$_2$R$_2$R$_1$R$_2$R$_2$R$_1$R$_1$R$_2$R$_2$GPILANLVSIV—COOH (SEQ ID NO:30),
$NH_2$—KKWWRRR$_1$R$_1$R$_2$R$_1$R$_1$R$_2$R$_2$GPALSNV—COOH (SEQ ID NO:31), or
$NH_2$—KKWWRRR$_1$R$_1$R$_2$GLKTAGPAIQSVLNK—COOH (SEQ ID NO:35)

wherein R$_1$ is a hydrophobic amino acid residue and R$_2$ is a hydrophilic amino acid residue. More specifically, the invention provides a method of inhibiting the growth of bacteria comprising contacting the bacteria with an inhibiting effective amount of a peptide of the invention, such as MBI 26 or MBI 29, $NH_2$—KWKSFIKKLTTAVKKVLTTGLPALIS—COOH (SEQ ID NO:1),
$NH_2$—KWKSFIKKLTSAAKKVVTTAKPLISS—COOH (SEQ ID NO:2), or
$NH_2$—KWKSFIKNLTKGGSKILTTGLPALIS—COOH (SEQ ID NO:3),
$NH_2$—KWKKFIKNLTKGGSKILTTGLPALIS—COOH (SEQ ID NO:4),
$NH_2$—KWKSFIKNLEKVLKPGGLLSNIVTSL—COOH (MBI 490) (SEQ ID NO:5),
$NH_2$—KWKSFIKNLEKVLKKGPILANLVSIV—COOH (MBI 491) (SEQ ID NO:6),
$NH_2$—KWKEFIKKLTTAVKKVLTTGLPALIS—COOH (MBI 492) (SEQ ID NO:7),
$NH_2$—KWKKFIKELQKVLAPGGLLSNIVTSL—COOH (MBI 493) (SEQ ID NO:8),
$NH_2$—KWKSFIKKLTSVLKKVVTTALPALIS—COOH (MBI 29A1) (SEQ ID NO:9),
$NH_2$—KWKSFIKNLTKVLKKVVTTALPALIS—COOH (MBI 29A2) (SEQ ID NO:10),
$NH_2$—KWKLFKKKGTGAVLTVLTTGLPALIS—COOH (MBI 29A3) (SEQ ID NO:11),
$NH_2$—KWKSFIKKLTSVLKKVVTTAKPLISS—COOH (SEQ ID NO:12),
$NH_2$—KKKSFIKLLTSAKVSVLTTAKPLISS—COOH (SEQ ID NO:13),
$NH_2$—KWKKFIKELQKVLKPGGLLSNIVTSL—COOH (SEQ ID NO:14),
$NH_2$—KKWWRRVLSGLKTGPALSNV—COOH (SEQ ID NO:15),
$NH_2$—KKWWRRVLKGLSSGPALSNV—COOH (SEQ ID NO:16),
$NH_2$—KKWWRRALQALKNGPALSNV—COOH (SEQ ID NO:17),
$NH_2$—KKWWRRVLSGLKTAGPAIQSVLNK—COOH (MBI 21A1) (SEQ ID NO:18),
$NH_2$—KKWWRRALQGLKTAGPAIQSVLNK—COOH (MBI 21A2) (SEQ ID NO:19),
$NH_2$—KKWWKAQKAVNSGPNALQTLAQ—COOH (SEQ ID NO:20)
$NH_2$—KKWWKAKKFANSGPNALQTLAQ—COOH (SEQ ID NO:21),
$NH_2$—KKWWKFIKKAVNSGTTGLQTLAS—COOH (SEQ ID NO:22),
$NH_2$—KKSFFKKLTSVASSVLS—COOH (MBI 21A14) (SEQ ID NO:23),
$NH_2$—WKVFKSFIKKASSFAQSVLD—COOH (SEQ ID NO:24), and
$NH_2$—KKWRKSFFKQVGSFDNSV—COOH (SEQ ID NO:25).

and analogs, derivatives, or conservative variations thereof.

The term "contacting" refers to exposing the bacteria to the peptide so that the peptide can effectively inhibit, kill, or lyse bacteria, bind endotoxin (LPS), or permeabilize gram-negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock. "Inhibiting" or "inhibiting effective amount" refers to the amount of peptide which is required to cause a bacteriostatic or bactericidal effect. Examples of bacteria which may be inhibited include *E. coli, P. aeruginosa, E. cloacae, S. typhimurium*, and *S. aureus*.

The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art. Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art. Further to the antibiotics listed above, typical antibiotics include aminoglycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

The peptides and/or analogues or derivatives thereof may be administered to any host, including a human or non-human animal, in an amount effective to inhibit not only growth of a bacterium, but also a virus or fungus. These peptides are useful as antimicrobial agents, antiviral agents, and antifungal agents. The peptides and/or analogues or derivatives thereof may be administered to any host, including a human or non-human animal, in an amount effective to inhibit not only growth of a bacterium, but also a virus or fungus. These peptides are useful as antimicrobial agents, antiviral agents, and antifungal agents.

The peptide of the invention can be administered parenterally by injection or by gradual infusion over time. The peptide can be administered intravenously, intraperitoneally, intramuscularly, subcutaneously, intracavity, or transdermally. Preferred methods for delivery of the peptide include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention provides a method of treating or ameliorating an endotoxemia or septic shock (sepsis) associated disorder, or one or more of the symptoms of sepsis comprising administering to a subject displaying symptoms of sepsis or at risk for developing sepsis, a therapeutically effective amount of a cationic peptide of the invention, for example, SEQ ID NO:1 or SEQ ID NO:2, or analogs, derivatives, or conservative variations thereof The term "ameliorate" refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza B, Neisseria meningitides*, staphylococci, or pneumococci. Patients at risk for sepsis include those suffering from gunshot wounds, renal or hepatic failure, trauma, burns, immunocompromised (HIV), hematopoietic neoplasias, multiple myeloma, Castleman's disease or cardiac myxoma.

The term "therapeutically effective amount" as used herein for treatment of endotoxemia refers to the amount of cationic peptide used is of sufficient quantity to decrease the subject's response to LPS and decrease the symptoms of sepsis. The term "therapeutically effective" therefore includes that the amount of cationic peptide sufficient to prevent, and preferably reduce by at least 50%, and more preferably sufficient to reduce by 90%, a clinically significant increase in the plasma level of TNF. The dosage ranges for the administration of cationic peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of cationic peptide, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature,* 330:662, 1987).

A patient who exhibits the symptoms of sepsis may be treated with an antibiotic in addition to the treatment with cationic peptide. Typical antibiotics include an aminoglycoside, such as gentamicin or a beta-lactam such as penicillin, or cephalosporin or any of the antibiotics as previously listed above. Therefore, a preferred therapeutic method of the invention includes administering a therapeutically effective amount of cationic peptide substantially simultaneously with administration of a bactericidal amount of an antibiotic. Preferably, administration of cationic peptide occurs within about 48 hours and preferably within about 2–8 hours, and most preferably, substantially concurrently with administration of the antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the peptides, they may also be used as preservatives or sterillants of materials susceptible to microbial or viral contamination. The peptides of the invention can be utilized as broad spectrum antimicrobial agents directed toward various specific applications. Such applications include use of the peptides as preservatives in processed foods (organisms including Salmonella, Yersinia, Shigella), either alone or in combination with antibacterial food additives such as lysozymes; as a topical agent (Pseudomonas, Streptococcus) and to kill odor producing microbes (Micrococci). The relative effectiveness of the cationic peptides of the invention for the applications described can be readily determined by one of skill in the art by determining the sensitivity of any organism to one of the peptides.

The following examples are intended to illustrate but not limit the invention. While they are typical of those that might be used, other procedures known to those skilled in the art may alternatively be used.

EXAMPLE 1

MIC VALUES FOR CATIONIC PEPTIDES

The minimum inhibitory concentrations of (MIC) of CEME, CEMA, the first 8 amino acid residues of CEME ($NH_2$—KWKLFKKIGIGAVLKVLTTGLPALIS—COOH; SEQ ID NO:1 with changes at residues 4, 6, 8–11, 14) and CEMA ($NH_2$—KWKLFKKIGIGAVLKVLTTGLPALKLTK—COOH; SEQ NO:1 with changes at residues 4,6,8–11, 14, and 25–28), (Piers, K. and Hancock, R., *Molec. Microbiology,* 12(6), 1994) 20 carboxy terminal amino acids of melittin (MA), 8 amino terminal amino acids from cecropin, and the peptides shown in SEQ ID NO:1, MBI 29 and SEQ ID NO:2, MBI 26, were determined for a number of different bacteria (Table 1a and 1b). Briefly, cells were grown overnight at 37° C. in LB-S (Luria broth without any salt supplement) and diluted one in 10,000 in the same medium to give concentrations of about $10^4$ to $10^5$ CFU/ml. The broth dilutions were set up in a 96 well microtiter plate by putting 200 µl of LB-S containing the initial concentration of antibiotic or compound in column 1 and 100 µl of the same medium in columns 2–12. The compounds were diluted by taking 100 µl of broth from column 1 and mixing it with column 2, resulting in a one in two dilution. This was continued to column 10. Finally, 10 µl of bacteria were pipetted into columns 1–11, and the plates incubated overnight at 37° C. The next day the plates were scored for growth in the wells, and the MIC determined.

TABLE 1a

MINIMUM INHIBITORY CONCENTRATION (MIC) VALUES FOR CATIONIC PEPTIDES

| STRAIN | CEME | CEMA | MBI 29 | MBI 26 | CE-8 | MA-20 |
| --- | --- | --- | --- | --- | --- | --- |
| *S. aureus* (K147) | 32 | ≧64 | 20 | ≧64 | ≧64 | ≧64 |
| *S. aureus* (SAP0017) | 24 | ≧64 | 18 | ≧64 | ≧64 | ≧64 |
| *S. epidermis* | 16 | ≧64 | 10 | ≧64 | ≧64 | ≧64 |
| *E. coli* (UB1005) | 5 | 10 | 3 | 3 | ≧64 | ≧64 |
| *P. aeruginosa* (H187) | 8 | 26 | 5 | 11 | ≧64 | ≧64 |
| *Candida albicans* (CAN105) | ≧64 | ≧64 | 40 | ≧64 | ≧64 | ≧64 |

Additional MICs were determined for MBI-26 and MBI-29 and MBI 29 and MBI 21 derivatives as noted for the following strains:

| Strain | MBI 26 | MBI 29 |
| --- | --- | --- |
| *P. aeruginosa* (H103) | 4 | 4 |
| *E. coli.* Bort | 2 | 6 |
| *E.coli* 0111:B4 | 2 | 2 |
| *X maltophilia* | 2 | 3 |
| *A. calcoaceticus* | 2 | 4 |
| *E. cloacae* | 2 | 2 |
| *K. pneumoniae* | 8 | 16 |

| Peptide | *E. coli* 0111:B4 µg/ml | *E. faecalis* | *B. Subtilis* | H103 | *S. epi* 0017 | SAP | K147 | C610 |
| --- | --- | --- | --- | --- | --- | --- | --- | --- |
| MBI29A1 | 4 | 64 | 16 | 16 | 16 | 16 | 16 | 8 |
| MBI29A2 | 8 | 64 | 8 | 16 | 16 | 8 | 16 | 8 |

TABLE 1a-continued

MINIMUM INHIBITORY CONCENTRATION
(MIC) VALUES FOR CATIONIC PEPTIDES

| | | | | | | | | |
|---|---|---|---|---|---|---|---|---|
| MBI29A3 | 8 | >128 | 16 | 16 | 16 | 32 | 32 | 8 |
| MBI21A1 | 16 | >128 | >128 | 64 | 128 | >128 | >128 | 16 |
| MBI21A2 | 32 | >128 | >128 | 128 | >128 | >128 | >128 | 16 |
| MBI21A14 | >128 | >128 | >128 | >128 | >128 | >128 | >128 | 128 |

In a separate set of experiments, the following MIC values were obtained:

TABLE 1b

MINIMUM INHIBITORY CONCENTRATION
(MIC) VALUES FOR CATIONIC PEPTIDES

| STRAIN | CEMA | CEMA$^{me}$ | MBI 29 | MBI 29$^{me}$ | MBI 26D | MBI 26L |
|---|---|---|---|---|---|---|
| S. aureus (K147) | ≧64 | ≧64 | 32 | 16 | ≧64 | ≧64 |
| S. aureus (SAP0017) | ≧64 | ≧64 | 32 | 16 | ≧64 | ≧64 |
| S. epidermis | 43 | 43 | 16 | 8 | 8–16 | 32 |
| P. aeruginosa (H187) | 32 | 53 | 16 | 8 | 16 | 32 |
| E. coli (UB1005) | 13 | 32 | 4 | 4 | 4–8 | 4 |
| E. faecalis | ≧64 | ≧64 | 32 | ≧64 | ≧64 | ≧64 |
| Candida albicans (CAN105) | ≧64 | ≧64 | 32 | 32 | ≧64 | ≧64 |

The results show that both MBI 29 (SEQ ID NO:1) and MBI 26 (SEQ ID NO:2) are effective antimicrobial agents for a variety of gram positive and gram negative bacteria In addition, all peptides were effective against *Candida albicans*. Modification of the peptides, such as methyl ester modification, or L to D amino acids provided a broader class of antimicrobial agents.

Agarose Dilution Susceptibility Testing

The following is a novel agarose-based solid phase assay system to measure antimicrobial activity of the cationic peptides of the invention, for example, either alone or in combination with a conventional antibiotic. Standard MIC methods, as described above or this method can be used to determine MICs of the peptides described herein.

A) Preparing plates

1) Unsupplemented Mueller-Hinton agarose (i.e. no Ca$^{2+}$ or Mg$^{2+}$ added) was used. (Unsupplemented broth is used with agar because agar contains divalent cations).

Prepared as follows:

22 g/L Mueller-Hinton powder (BBI, #11443)

15 g/L agarose (Sigma, A-0576)

QS to 1 L with sdH$_2$O

Heat to boiling and boil 1 min

Adjust pH to 7.3 with NaOH or KOH (adjust the meter to the correct temperature

—note agarose solidifies at <40° C.)

Autoclave for 10 min at 121 ° C.

After the agarose has been autoclaved, it is allowed to cool to 40–45° C. in a water bath before aseptically adding antimicrobial solutions, and pouring the plates.

2) Appropriate dilutions of antimicrobial solutions are added to molten test agarose that has been allowed to equilibrate in a water bath to 40–45 ° C. In general, a scheme in which 1 part of antimicrobial solution is added to 9 parts of liquid agarose is used (i.e. 2 mL of drug to 18 mL of agar for each plate; I mL of each drug in the combination if testing synergy).

3) The agarose and antimicrobial solution are mixed throughly by gentle inversion about 10x to avoid bubbles and the mixture poured into petri-dishes on a level surface to result in an agar depth of 3–4 mm.

4) The plates are poured as quickly as possible after mixing to prevent cooling and partial solidification.

5) The agarose is allowed to solidify at room temperature and the plates are either used immediately or stored in sealed plastic bags at 4° C. Storage time can vary but plates should be used within a week.

6) Plates stored at 4° C. should be allowed to equilibrate at room temperature before use. The surface should be dry before inoculating the plates. If necessary, plates can be placed in the fume hood for 30 min with lids ajar to hasten drying of agarose surface.

B) Inoculum Preparation

1) To standardize the inoculum density, a 0.5 McFarland standard can be prepared as follows:

A 0.5 mL aliquot of 0.48 m BaCl$_2$ is added to 99.5 mL of 0.36 N H$_2$SO$_4$ (1% v/v) with constant stirring to maintain a suspension. The correct density should be verified using a spectrophotometer with a 1 cm light path and matched cuvettes to determine the absorbance. The absorbance at 630 nm should be 0.08 to 0.10. The suspension should be transferred to 10 mL aliquot into screwcap tubes of the same size as those used in growing or diluting the bacterial inoculum. These tubes should be tightly sealed and stored in the dark at room temperature. The turbidity standard should be rigorously agitated on a vortex mixer prior to use. If large particles appear, the standard should be replaced. Replacement should occur every month (use a new standard tubes each time, and when ten are used up, make a new batch).

2) 3 to 5 morphologically identical colonies are selected from a TSA plate (the top of each is touched with a sterile loop) and transferred to a tube of 5 mL TSB.

3) The broth culture is incubated at 37° C. with shaking until it achieved or exceeds the turbidity of the standard (2 to 6 hours) -approx. 1 to $2\times10^8$ CFU/mL.

4) The turbidity can be adjusted with broth to obtain a turbidity equal to the 0.5 standard. Use adequate lighting and hold up a white card with black lines behind the cultures to assist in the comparison.

5) Cultures adjusted to the standard are diluted 1/10 in sterile broth to obtain a density of approximately $10^7$ CFU/mL. Most inoculum replicators deposit approximately 1 to 2 µL on the agarose surface. The final inoculum on the agarose will then be approximately $10^4$ CFU in a spot of 5 to 8 mm in diameter on the agarose. The adjusted suspensions should be used for final inoculation within 15 min of preparation.

The tubes containing the adjusted and diluted bacterial suspensions should be arranged in order on a rack. An aliquot of each well-mixed suspension is placed into the corresponding well in the replicator inoculum block. The agarose plates are marked for orientation of the inoculum spots. A growth control plate (no antimicrobial) is inoculated first and then, starting with the lowest concentration, the plates continuing the different antimicrobial concentration are inoculated (Optional—A second growth control plate is inoculated last to ensure that there was no contamination or significant antimicrobial carryover during the inoculation). Optional—a sample of each inoculum is streaked on a suitable agar plate and incubated 6) The inoculated plates are allowed to stand at room temperature until the moisture in the inoculum spots have been absorbed into the agarose. The plates are inverted and incubated at 35 ° C. for 24 hours, 48 hours.

7) The plates should be placed on a dark, nonreflecting surface to determine the end points. The MIC is recorded as the lowest concentration of antimicrobial agent that completely inhibits growth, disregarding a single-colony or a faint haze caused by the inoculum.

8) If two or more colonies persist in concentrations of the agent beyond an obvious end point, or if there is no growth at lower concentrations, the culture purity is checked and test possibly repeated.

9) After 48 hours a replica plating tool can be used to transfer cells onto a fresh TSA or BHI plate and growth is read after 24 hrs.

EXAMPLE 2

EFFECT OF FORMULATION ON BACTERICIDAL ACTIVITY

Effect of formulation on bactericidal activity and MIC was determined using the test solutions listed below. The results show that citrate and related formulations reduced the MIC (Table 2). Similar effects were seen with acetate formulated peptide (Tables 2 and 3).

TABLE 2

EFFECT OF CITRATE, ASCORBIC ACID AND DEXTROSE ON MBI 26 (10 MG/ML) KILLING OF *P. AERUGINOSA*

| Test Solution | Peptide | Survivors at Time (min.) | | | |
|---|---|---|---|---|---|
| | | 0 | 15 | 30 | 60 |
| Citrate (0.129M) | Control | $1.1 \times 10^7$ | $1.1 \times 10^7$ | $1.2 \times 10^7$ | $1.4 \times 10^7$ |
| | + MBI 26 | $1.1 \times 10^7$ | 0 | 0 | 0 |
| Citrate (0.129M) + Ascorbic | Control | $1.3 \times 10^7$ | $1.2 \times 10^7$ | $1.7 \times 10^7$ | $1.7 \times 10^7$ |
| | + MBI 26 | $1.3 \times 10^7$ | 0 | 0 | 0 |

TABLE 2-continued

EFFECT OF CITRATE, ASCORBIC ACID AND DEXTROSE ON MBI 26 (10 MG/ML) KILLING OF *P. AERUGINOSA*

| Test Solution | Peptide | Survivors at Time (min.) | | | |
|---|---|---|---|---|---|
| | | 0 | 15 | 30 | 60 |
| Acid (100 mM) Citrate-Dextrose | Control | $1.2 \times 10^7$ | $5.8 \times 10^6$ | $6.9 \times 10^6$ | |
| | + MBI 26 | $9 \times 10^6$ | 20 | 0 | 0 |
| Citrate-Phosphate Dextrose | Control | $7.8 \times 10^6$ | $6.5 \times 10^7$ | $1.5 \times 10^7$ | $1.1 \times 10^7$ |
| | + MBI 26 | 0 | | 0 | 0 |
| Dextran | Control | $2.3 \times 10^7$ | $2.2 \times 10^7$ | $1.4 \times 10^7$ | $2 \times 10^7$ |
| | + MBI 26 (20 µg) | $1.9 \times 10^7$ | $1.2 \times 10^6$ | $1 \times 10^6$ | $8.5 \times 10^5$ |

TABLE 3

EFFECT OF CITRATE ADDITION TO CATION ADJUSTED MEDIA ON MINIMAL INHIBITORY CONCENTRATIONS

| | MIC (µg/mL) | |
|---|---|---|
| Strain | CAMHB | CAMHB + Citrate |
| *E. coli* (UB1005) | 4 | 2 |
| *E. coli* (111:B4) | 8 | 2 |
| *E. coli* (Bort) | 16 | 8 |
| *S. typhimurium* (C610) | 8 | 2 |
| *E. facaelis* (C625) | 16 | >32 |
| *A. calcoacet.* (C402) | 8 | 4 |
| *A. calcoacet* (C403) | 1 | 1 |
| *E. cloacae* (C601) | 8 | 4 |
| *E. cloacae* (C602) | 8 | 4 |
| *E. cloacae* (C603) | 4 | 2 |
| *P. aeruginosa* (H103) | 16 | 2 |

The media used in this experiment was Cation Adjusted Muller Hinton (CAMHB), and CAMHB + 8 mM citrate. MBI 26 was prepared in sterile distilled water.

EXAMPLE 3

INNER MEMBRANE PERMEABILIZATION

Figure 3:
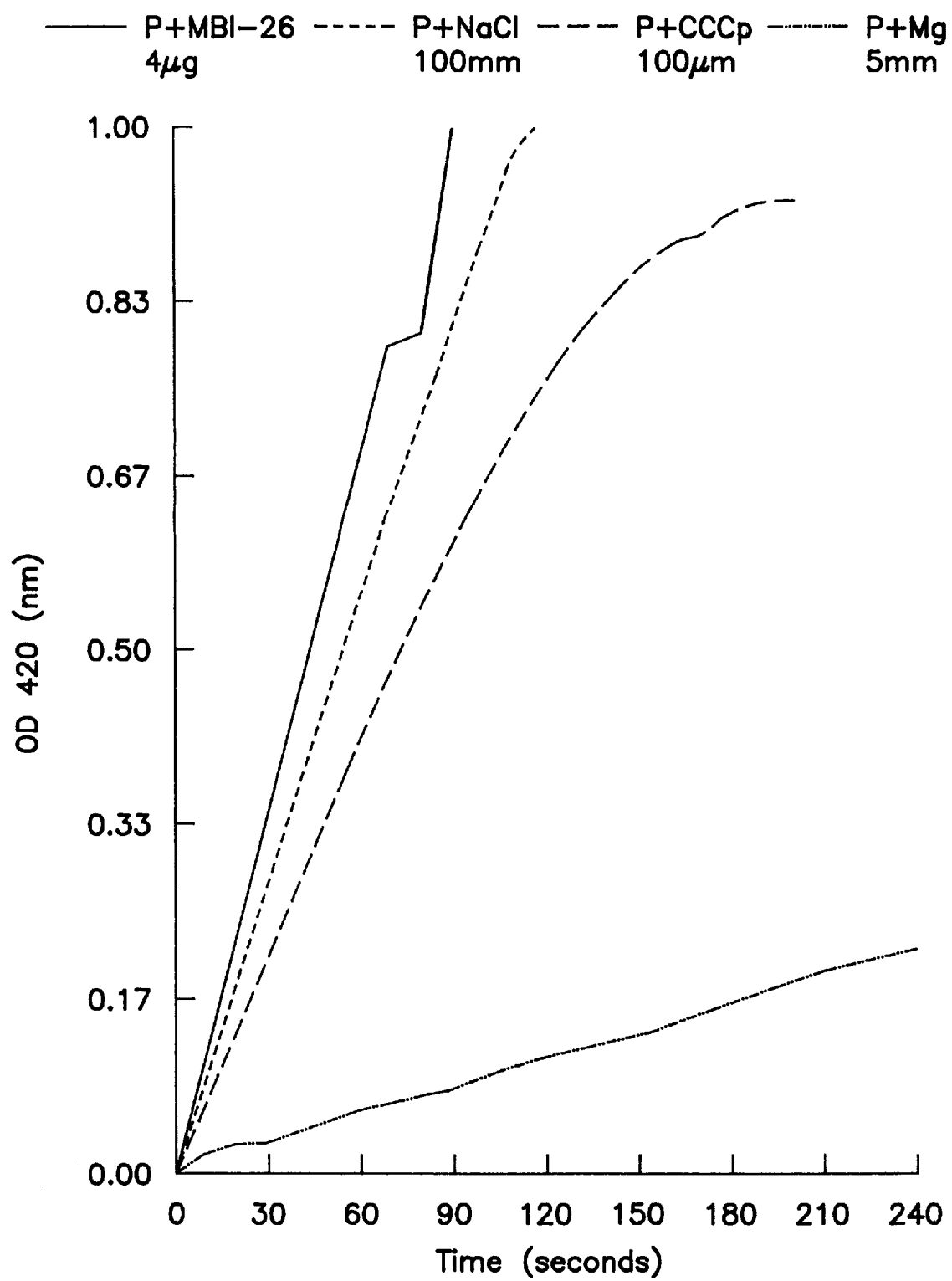
FIG. 3 shows an inner membrane permeabilization assay for MBI 26.
Figure 4:
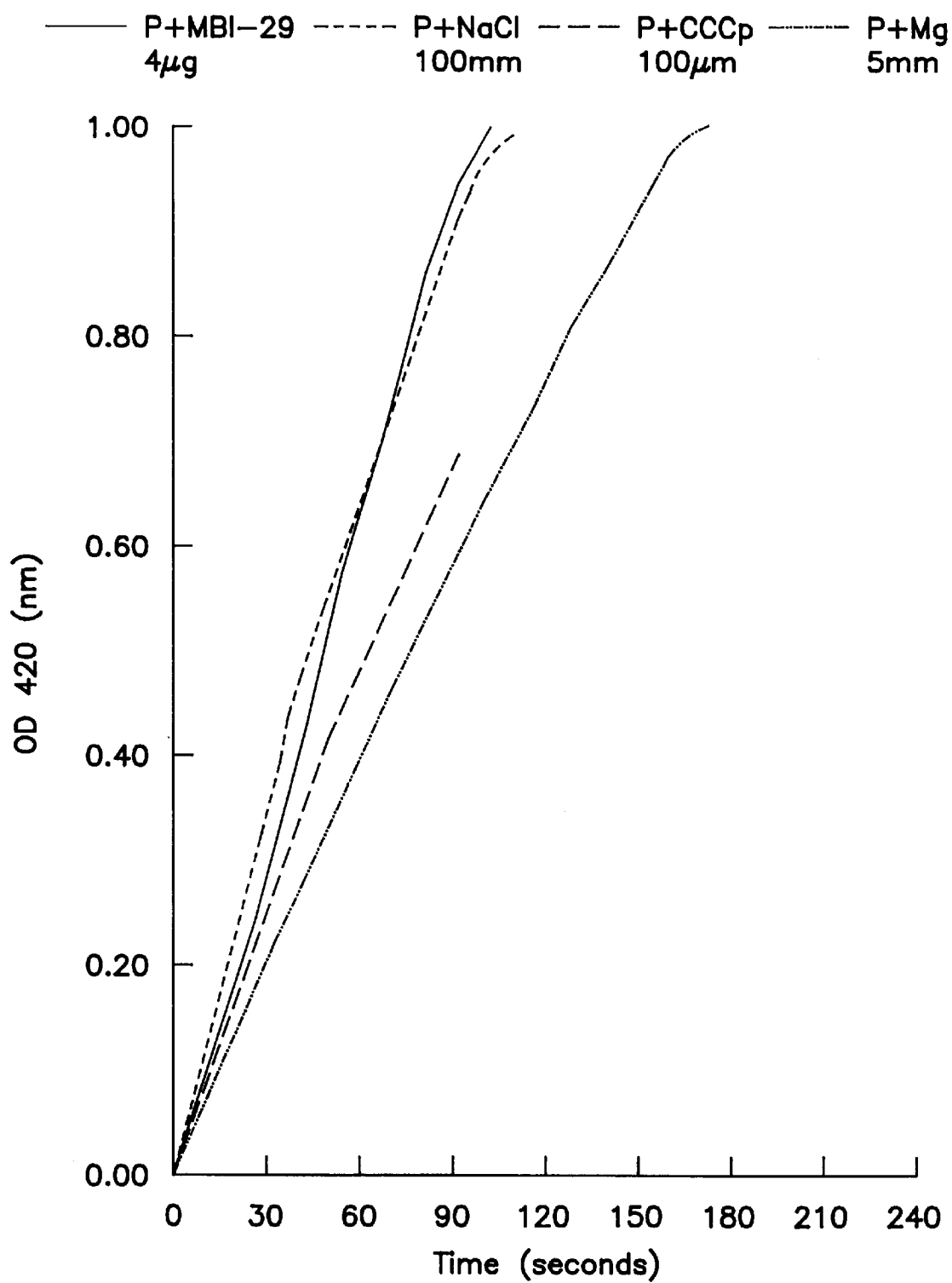
FIG. 4 shows an inner membrane permeabilization assay for MBI 29.

Inner membrane permeability was determined by measurement in *E. coli* ML 35 of β-galactosidase activity using ONPG as a substrate. Normally ONPG cannot pass across the cytoplasmic membrane to permit hydrolysis by the cytoplasmic enzyme β-galactosidase. However, cationic peptides, by permeabilizing the inner membrane, unmasks this enzyme leading to color development as ONP is released. MBI 26 and MBI 29 were tested with the same conditions as shown in FIGS. 3 and 4 (4 ug MBI 26 or MBI 29 alone,■; +100 mM NaCl, □; +100 uM CCCP, ■; +5 mM Mg, ▪▪▪. While 100 mM NaCl had little effect on MBI 26 permeabilization, 5 mM Mg++ had a large inhibitory effect. MBI 29 permeabilization of the inner membrane was the least affected by any of the conditions especially $Mg^{++}$ as seen in FIG. 4. Addition of citrate increased the lag time before the peptides were able to permeabilize the membranes. When the experiments were executed in cation adjusted media (CAMHB), the lag time was increased up to 30 minutes. The data in Table 4 shows the rate and lag time for inner membrane permeabilization of MBI 26, MBI 29 and peptides 490, 491, 492 and 493 (SEQ ID NO:2, 1, and 5–8, respectively).

TABLE 4

INNER MEMBRANE PERMEABILIZATION

| Peptide | Lag Time (Sec.) | Rate of Hydrolysis ($\Delta$AU min$^{-1}$) |
| --- | --- | --- |
| MBI 26 (SEQ ID NO:2) | 210 | 0.081 |
| MBI 29 (SEQ ID NO:1) | 66 | 0.21 |
| 490 (SEQ ID NO:5) | 156 | 0.081 |
| 491 (SEQ ID NO:6) | 152 | 0.14 |
| 492 (SEQ ID NO:7) | 68 | 0.23 |
| 493 (SEQ ID NO:8) | 136 | 0.14 |

EXAMPLE 4

INHIBITION OF LPS-MEDIATED TNF INDUCTION IN MACROPHAGES BY CATIONIC PEPTIDES

The effect of cationic peptides, CEME (KWKLFKKIGIGAVLKVLTTGLPALIS (SEQ ID NO:36)) and CEMA (KWKLFKKIGIGAVLKVLTTGLPALKLTK (SEQ ID NO:37)) and the peptides of the invention, MBI 29, NH$_2$—KWKSFIKKLTTAVKKVLTTGLPALIS—COOH (SEQ ID NO:1) and MBI 26, NH$_2$—KWKSFIKKLTSAAKKVVTTAKPLISS—COOH (SEQ ID NO:2), on LPS-induced TNF in macrophages was examined. RAW 264.7 macrophage cells were grown by seeding 10$^6$ cells into a 162 cm$^2$ cell culture flask and incubated at 37° C., 5% CO$_2$ for 1 week. RAW cell media [(Dulbecco's Modified Eagle Medium with Hepes buffer 450 ml; 2.4 mM L-glutamine 3 ml (400 mM); Pen/Strep 3 ml (10$^4$U/ml of Pen, 1 mg/ml strep); and 10% heat inactivated fetal bovine serum (FBS) 50 ml)] was then completely removed from flasks. 10 mls of cell dissociation solution (Sigma) was added to each flask and incubated at 37° C. for 10 minutes. Cells were removed from flasks, diluted in RAW cell media and centrifuged for 6 minutes. The cell pellet was resuspended in 5 ml of media/flask used. 100 μl cell suspension was removed and added to 400 μl of trypan blue and cells were counted using a hemocytometer. The cell suspension was diluted to 1×10$^6$ cells/ml and 1 ml of suspension was added per well of a 24 well plate. The 24 well plates were incubated at 37° C., 5% CO$_2$ overnight for use in the assay.

After an overnight incubation, the media was aspirated from all the wells. 1 00 μl of Lipopolysaccharide (LPS) was added at 100 ng/100 μl. CEME, CEMA or MBI 29 was added at the desired concentration/100 μl to specified wells. RAW cell media was added to all the wells so they all had a final volume of 1 ml. The plates were then incubated for six hours at 37° C., 5% CO$_2$. The supernatant was then removed from the wells and stored overnight at 4° C. For those wells in which whole bacteria were added directly to the wells, the supernatant was centrifuged in 0.2 μm filter eppendorf tubes for 5 minutes.

The supernatants were then used in cell cytotoxic L929 assay. The samples were transferred to 96 well plates. 50 μl of TNF media was added to all the wells in all the plates except to those wells in the first row. 10 μl of murine TNF standard (20 ng/ml) and 90 μl of TNF media was added in duplicate to the plate and diluted 1:2 down the plate to the second to last row. Test samples (75 μl), comprising the supernatants from the RAW cell assays, were added to separate rows in duplicate and diluted 1:3 to the second to last rows.

TNF-sensitive L929 mouse fibroblast cells were grown by seeding 10$^6$ cells into a 162 cm$^2$ cell culture flask and left to grow for 1 week. L929 cells were removed from the flask with 10 mls of trypsin-EDTA/flask and incubated 3–5 minutes. Cell suspension was diluted and centrifuged for 6 minutes. The pellet was resuspended in 5 mls of fresh L929 media/flask and counted (same as RAW cells). Cell suspension was diluted to 10$^6$ cells/ml. 100 μl was used to inoculate each well of the 96 well plates with the supernatants. (L929 Growth Media was the same as RAW cell media except instead of FBS, 50 mls of 10% heat inactivated horse serum was utilized; TNF Assay Media was the same as RAW cell media except 4 μg/ml Actinomycin D was added.)

The plates were incubated at 37° C. at 5% CO$_2$ for 2 days. The media was then aspirated and replaced with 100 μl of the dye MTT (0.5 mg/ml) in modified Eagle Medium without phenol red. The plates were then incubated at 37° C. at 5% CO$_2$ for 3 hours. The dye was then removed and replaced with 100 μl of absolute ethanol. The plates were left at room temperature for 10–15 minutes to dissolve the formazan dye crystals.

The plates were read at 570 nm in a ELISA plate reader with 690 nm reference filter. One unit of TNF activity is defined as the amount required to kill 50% of the L929 cells. The TNF level in Units per ml therefore was the reciprocal of the dilution which led to a 50% killing of L929 cells.

Figure 5A:
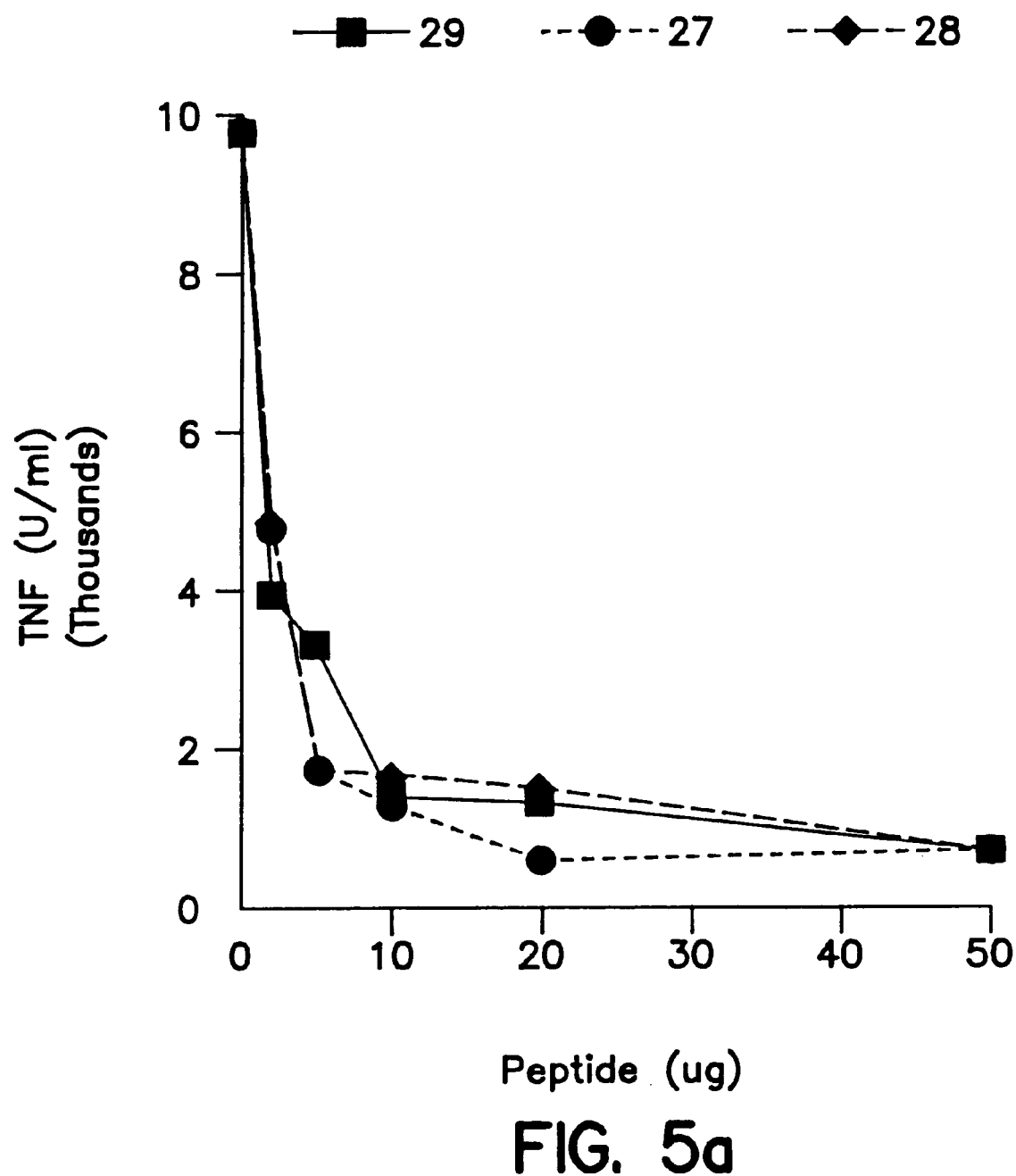
FIG. 5a shows tumor necrosis factor (TNF) levels measured 6 hours after the addition of *E. coli* 0111:B4 LPS and CEME (ME), CEMA (MA), and MBI 29 to macrophage cells. The data is from two separate assays.
Figure 5B:
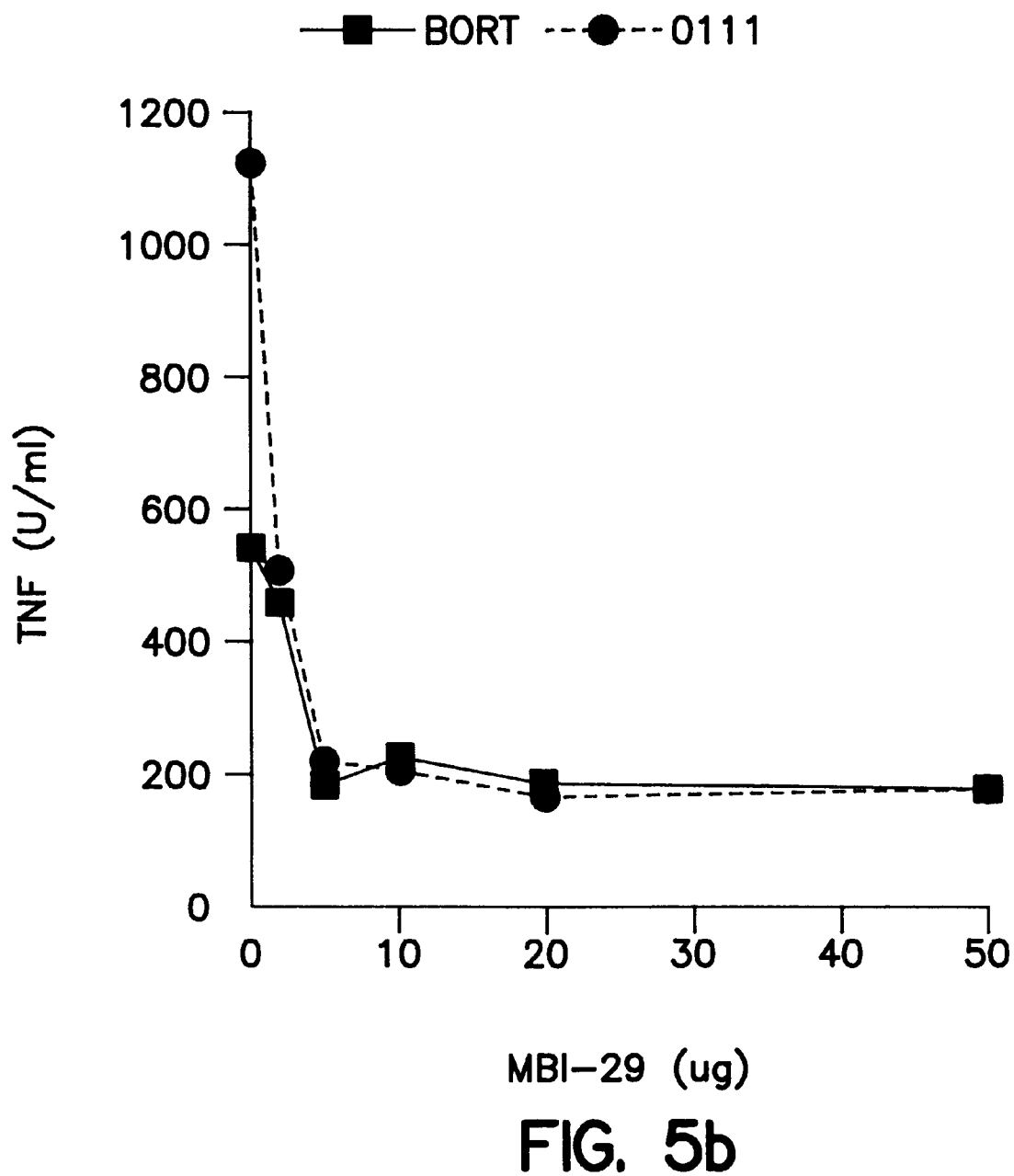
FIGS. 5b and 5c show tumor necrosis factor (TNF) levels measured 6 hours after the addition of *E. coli* Bort LPS and *E. coli* 0111:B4 LPS and MBI 29 to macrophage cells. The data is from two separate assays.
Figure 5C:
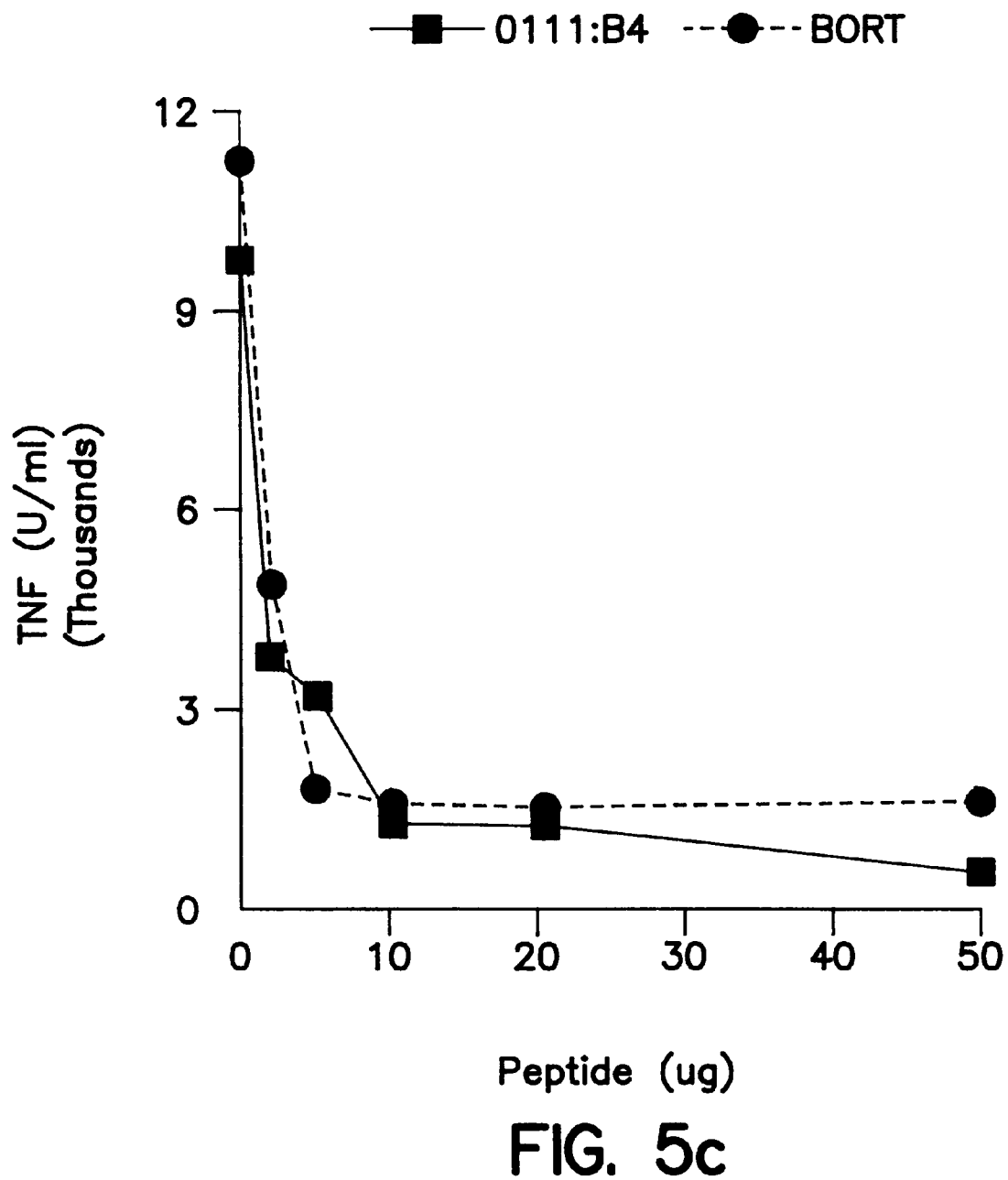
Figure 6A:
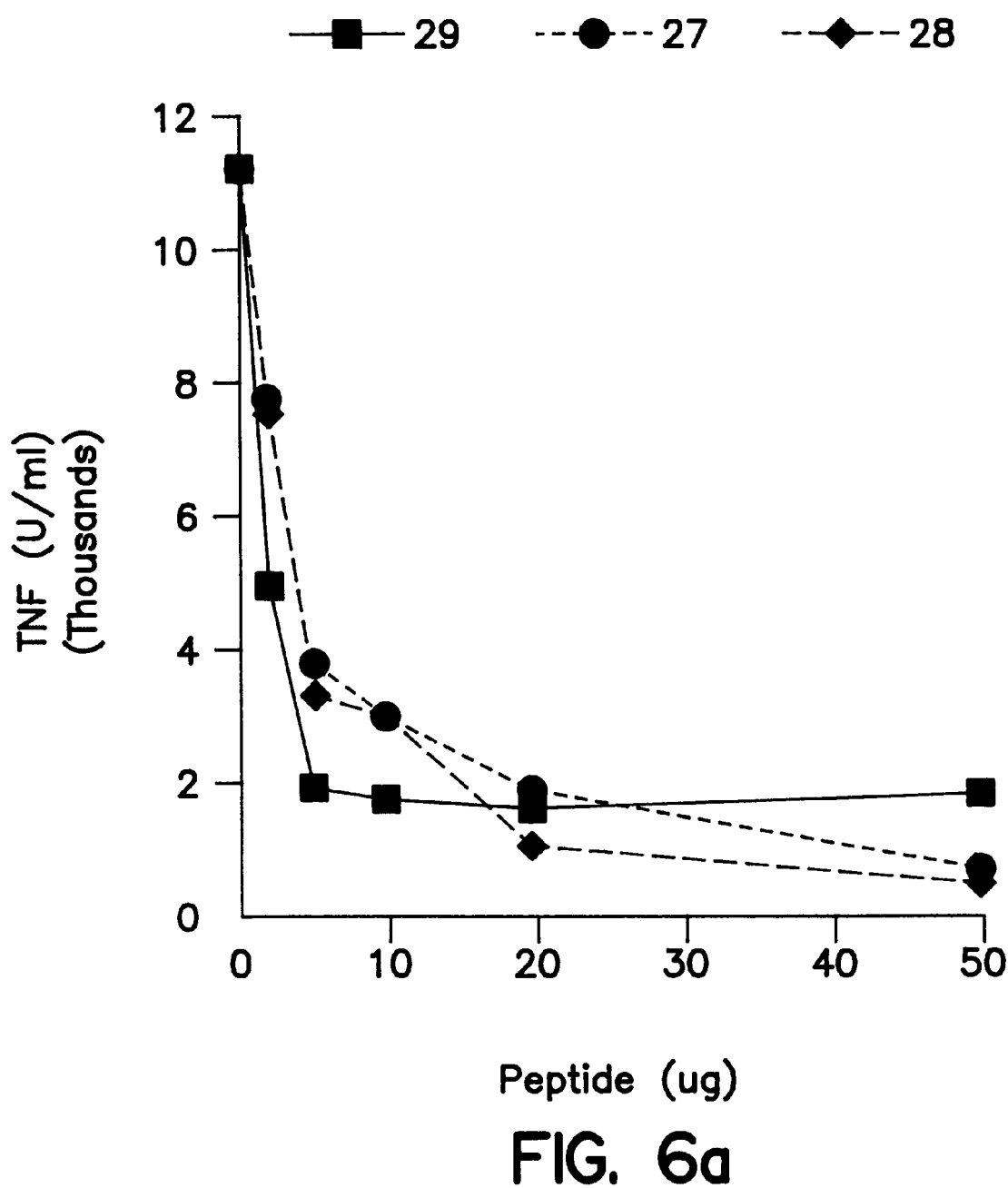
FIG. 6a shows tumor necrosis factor (TNF) levels measured 6 hours after the addition of *E. coli* Bort LPS and CEME (ME), CEMA (MA) and MBI 29 to macrophage cells. The data is from two separate assays.
Figure 6B:
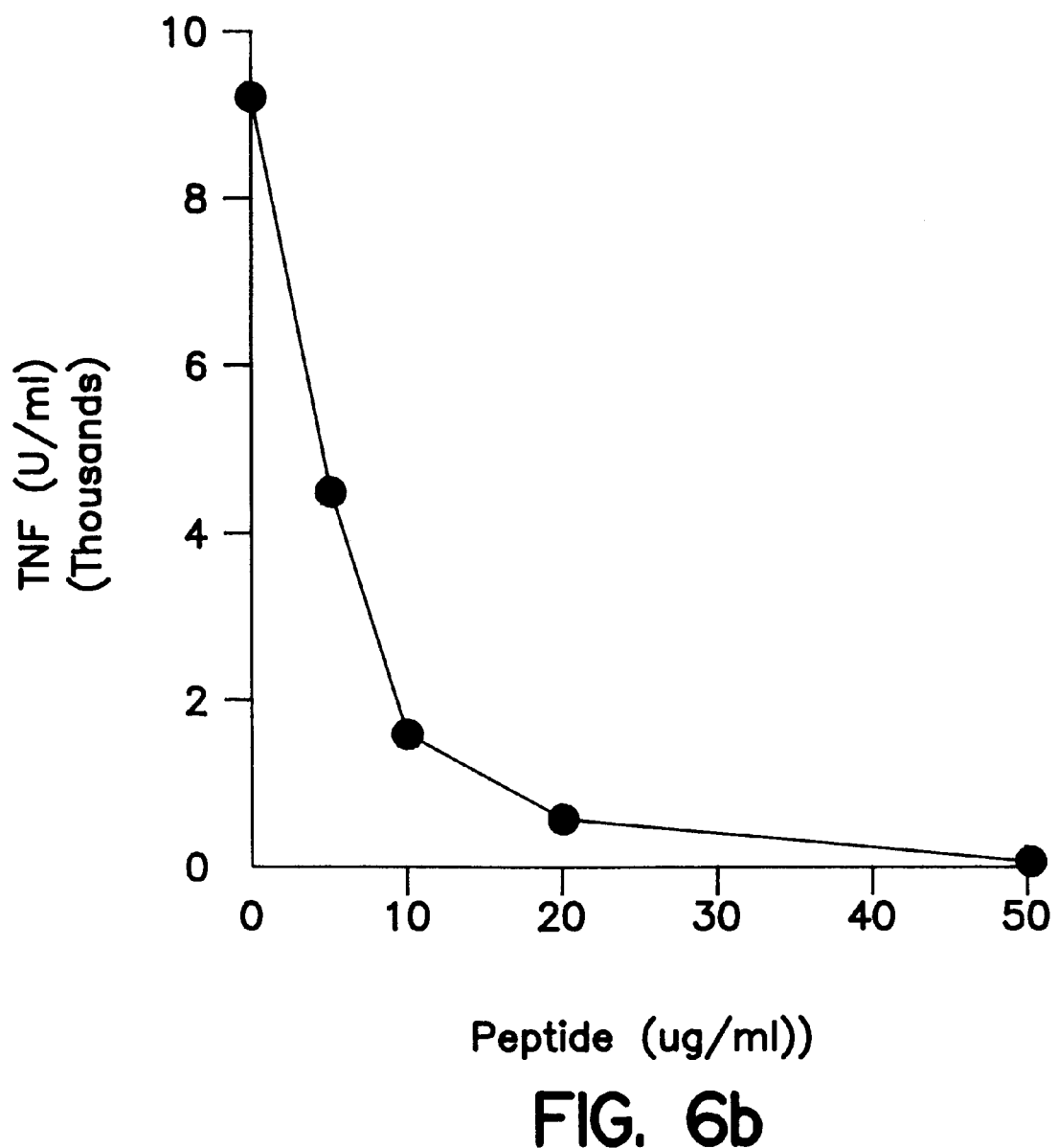
FIG. 6b shows tumor necrosis factor (TNF) levels measured 6 hours after the addition of *P. aeruginosa* LPS and MBI 26 to RAW macrophage cells.
Figure 6C:
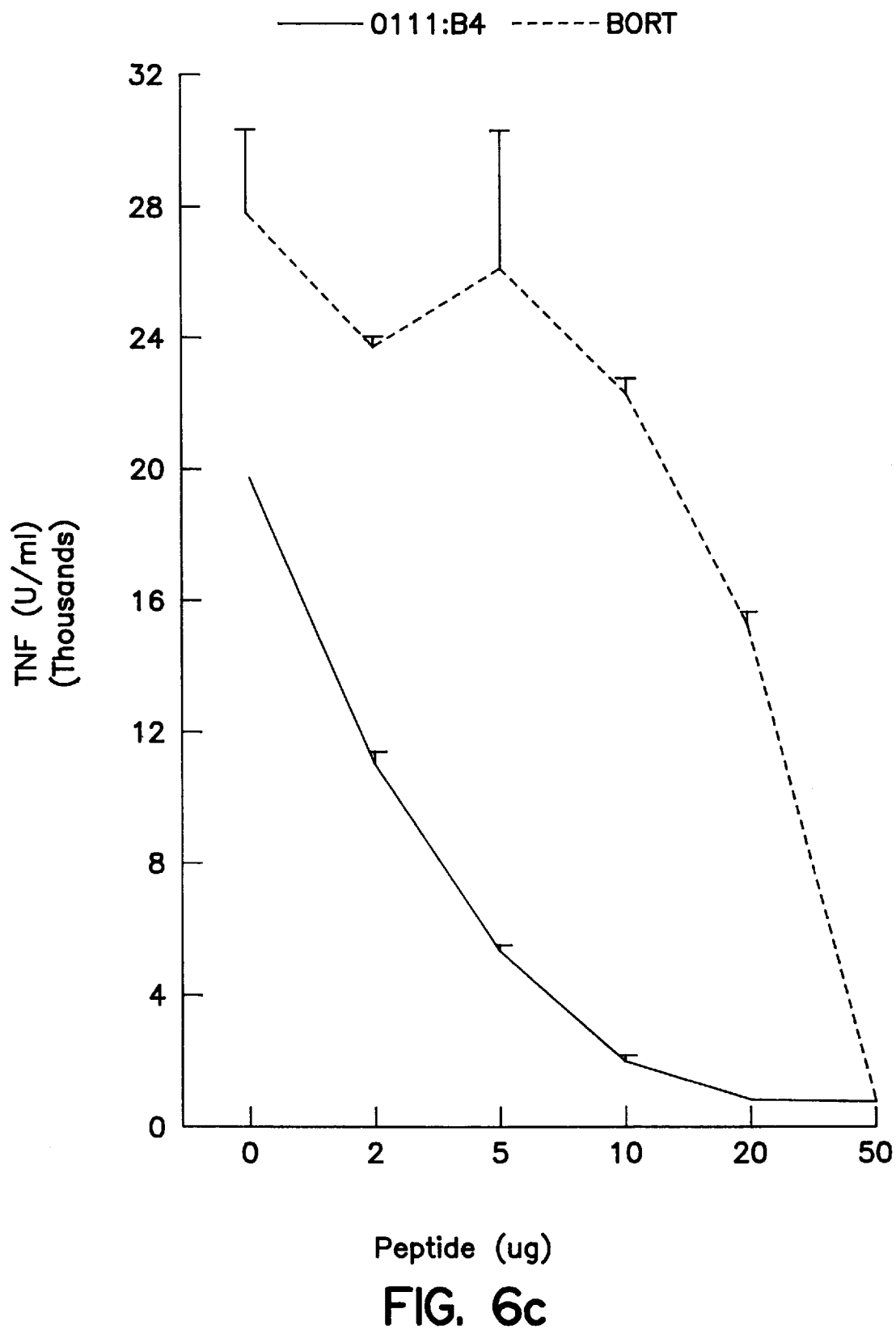
FIG. 6c shows tumor necrosis factor (TNF) levels measured 6 hours after the addition of *E. coli* Bort LPS, *E. coli* 0111:B4 LPS and MBI 26 to RAW macrophage cells.

FIGS. 5 and 6 show levels of TNF (U/ml) after a 6 hour treatment with increasing amounts (0, 5, 10,20, 30,40 or 50 μg) of either CEME (ME), CEMA (MA), MBI 26 (SEQ ID NO:2) or MBI 29 (SEQ ID NO:1) peptide and 100 ng of LPS. TNF levels were measured six hours after the addition of E. coli 0111:B4 or E. coli Bort LPS (FIGS. 5a, 5b, 5c and FIGS. 6a and 6c as labeled). P. aeruginosa LPS was also added in FIG. 6b. The data shows the results of several separate experiments and indicate that both peptides efficiently reduce the level of LPS-induced TNF in the culture with three distinct LPS samples at concentrations of peptides as low as 5 μg/ml.

In addition, the peptides of SEQ ID NO:5–8 also bound effectively to LPS with high affinity based on Dansyl polymyxin displacement assays (Table 5).

TABLE 5

| Peptide | I$_{50}$ (mM) | I$_{max}$ (%) |
| --- | --- | --- |
| MBI 26 (SEQ ID NO:2) | 1.8 | 38 |
| MBI 29 (SEQ ID NO:1) | 2.8 | 40 |
| 490 (SEQ ID NO:5) | 4.9 | 40 |
| 491 (SEQ ID NO:6) | 4.5 | 24 |
| 492 (SEQ ID NO:7) | 5.4 | 48 |
| 493 (SEQ ID NO:8) | 3.8 | 56 |

EXAMPLE 5

CATIONIC PEPTIDE REDUCTION OF LPS-INDUCED TNF

Figure 7A:
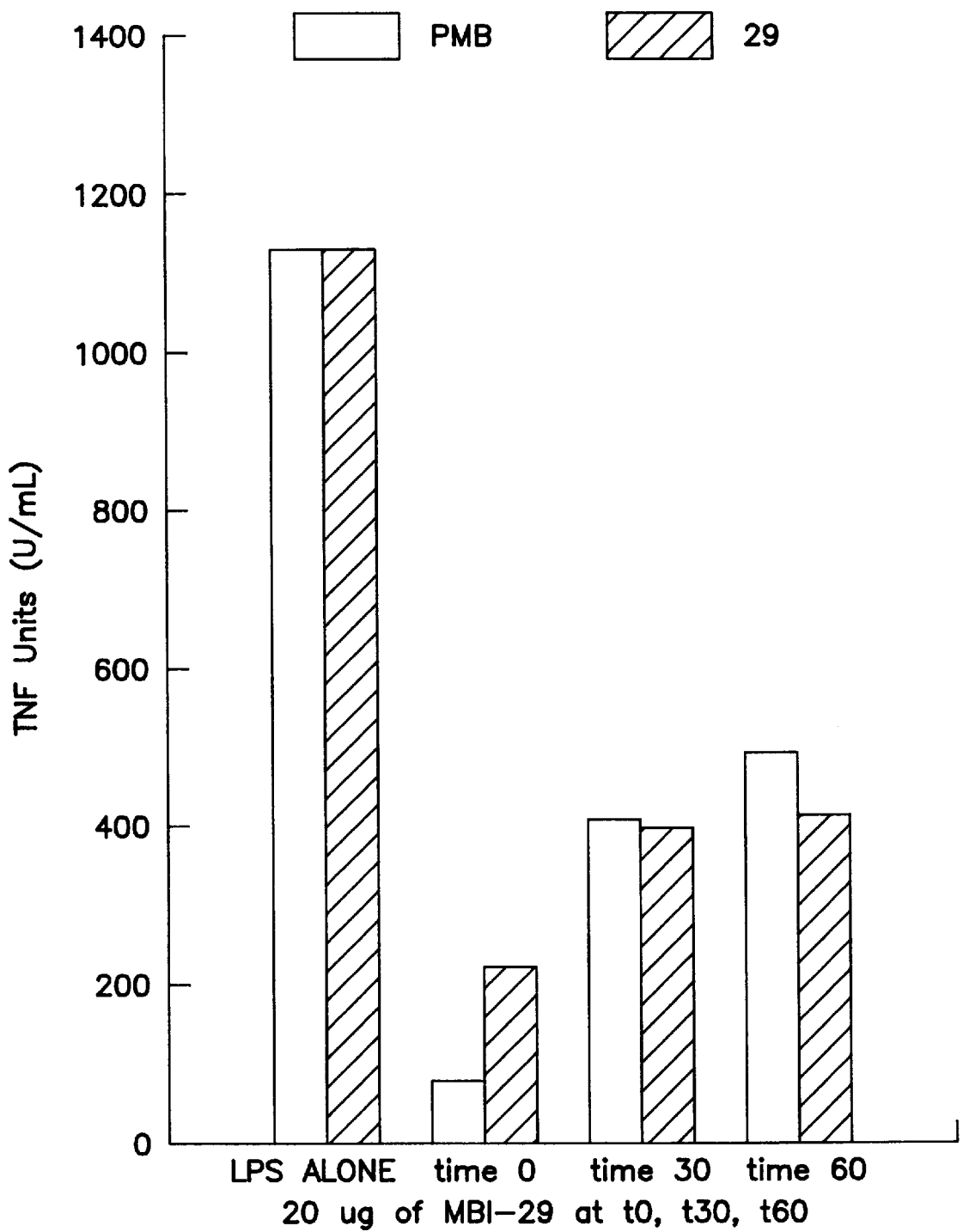
FIGS. 7a and 7b show RAW cell TNF production after addition of E. coli 0111:B4 LPS and the effect of the addition of MBI 29 and polymyxin B on TNT.
Figure 7B:
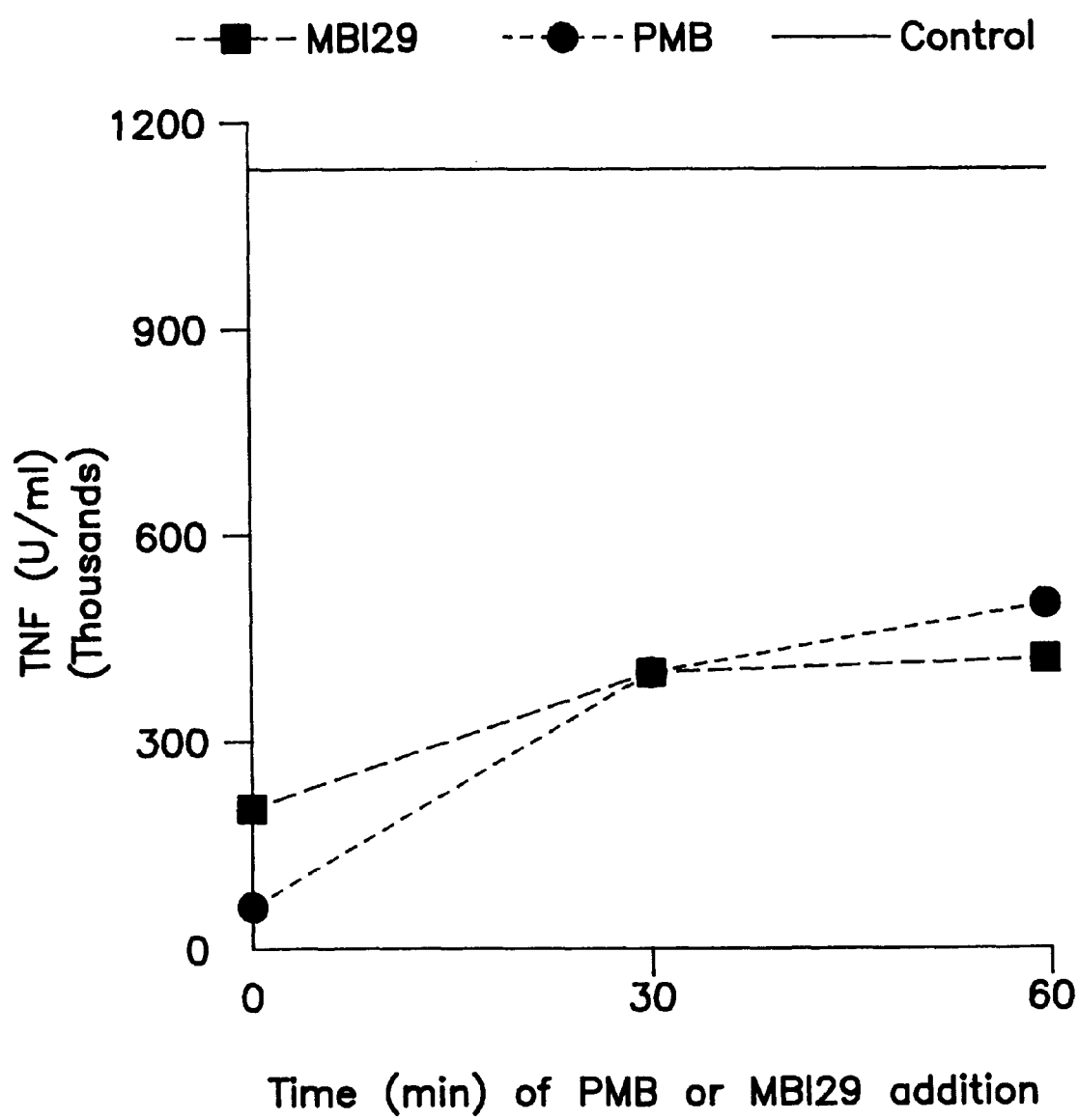

In order to determine how rapidly the cationic peptides reduced LPS-induced TNF production, E. coli 01111:B4 was added at time 0 to RAW macrophages. MBI 29 or Polymyxin B was added at time 0, 30 and 60 minutes. Levels of TNF were measured after 6 hours. The results are shown in FIGS. 7a and 7b(PMB, Polymyxin B; 29, MBI 29 (SEQ ID NO:1)). The results show that MBI 29 inhibited TNF induction by LPS in a similar manner to polymyxin B. Furthermore, MBI 29 was effective at reducing the ability of LPS to induce TNF in RAW cell lines even when added 60 minutes after the addition of LPS. MBI 29 demonstrated a distinct and reproducible advantage over polymyxin B when added 60 minutes after the addition of LPS. To confirm that MBI 29 was acting on LPS rather than directly upon macrophage cell lines, 20 μg of MBI 29 was added to RAW cells and incubated for 60 minutes prior to aspiration of the medium and washing the cells 3 times with HBSS (Hanks Buffered Salt Solution). Addition of 10 ng or 100 ng of LPS to the washed RAW cells resulted in a high level of TNF induction (14,000–20,000 Units of TNF per ml), suggesting that the MBI 29 had not permanently depressed the ability of RAW cells to induce TNF in response to LPS addition. In contrast, the aspirated medium containing MBI 29 could depress the ability of fresh RAW cells to induce TNF in response to 10 ng or 100 ng of E. coli LPS by 98.5% and 75% respectively. Up to 50 μg of MBI 29 caused no apparent decrease in RAW cell viability as judged by Trypan blue exclusion.

EXAMPLE 6

PROTECTION FROM LETHAL LPS ENDOTOXICITY IN A MOUSE ENDOTOXIC SHOCK MODEL

The ability of MBI 29 and MBI 26 to protect against LPS-induced endotoxemia is assessed in vivo. Mice (8–10 weeks old) are injected intraperitoneally with 20 μg D-galactosamine (Dgal) to sensitize them to LPS according to the method of Galanos (Galanos, et al., *Proc. Natl. Acad. Sci., USA,* 76:5939–5943, 1979), followed by 0, 50, 100, or 200 μg MBI 29 or MBI 26 in 100 μl. Immediately afterwards LPS (10 or 20 μg) in 100 μl is injected. The mice are observed at 24 and 48 hours after injections and survivors noted. MBI 26 was shown to be non-toxic up to 30.6 mg/kg in mice.

To demonstrate that survival is associated with a reduction in TNF levels, 10 μg of LPS and 20 mg of Dgal are injected at time 0. Thirty minutes later, the mice are sacrificed and the blood is taken and centrifuged to separate the serum which was used in the cell cytotoxic L929 assay. The results suggest that the bactolysins have potential in therapy against endotoxin-associated disorders.

EXAMPLE 7

CHARACTERIZATION OF DERIVATIVE PEPTIDES

Peptides 490–493 (SEQ ID NO:5–8) were found to possess comparable anti microbial activity to MBI 26 and MBI 29 (Table 6). These peptides do not lyse Red Blood Cells at concentration below 55 μg/mL.

TABLE 6

| Peptide | MIC (μg/mL) E. coli (UB 1005) | P. aeruginosa (H187) | RBC Lysis (μg/mL) |
|---|---|---|---|
| MBI 26 | 1.1 | 4.5 | >55 |
| MBI 29 | 0.5 | 1.0 | >55 |
| 490 | 1 | 8 | >55 |
| 491 | 2 | 8 | >55 |
| 492 | 2.4 | 4.8 | >55 |
| 493 | 5 | 10 | >55 |

α Helical Content of Cationic Peptides by CD Spectra

The α helical content of the peptides were measured in buffer, liposomes and 20% Hexafluoroisopropanol (HFPIP). The liposomes constituted of POPC alone or POPC and POPC and 30% POPG (Table 7).

TABLE 7

| | % α helicity | | | |
|---|---|---|---|---|
| Peptide | Buffer | POPC Liposomes | POPC/POPG Liposomes | 20% HFIP |
| MBI 26 | 0 | 0 | 8 | 70 |
| MBI 29 | 0 | 16 | 8 | 50 |
| 490 | 0 | 29 | 27 | 41 |
| 491 | 0 | 0 | 15 | 44 |
| 492 | 0 | 42 | 19 | 48 |
| 493 | 0 | 18 | 20 | 42 |

EXAMPLE 8

SYNERGISM BETWEEN CATIONIC PEPTIDES AND ANTIBIOTICS

Synergy between the peptides of the invention and conventional antibiotics from several different classes was determined by MIC and FIC values. The following Tables 8–47 show the MIC and FIC values for MBI 26 and MBI 29 with different bacteria (*A. calcoaceticus, P. aeruginosa, E. cloacae* and *X. maltophila*) and different classes of antibiotics. Synergism is identified as an FIC of about ≦0.5.

TABLE 8

Synergy of MBI-26 + Ciprofloxacin against *A. calcoaceticus*

| Isolate Number | Strain Number | MIC (μg · mL$^{-1}$) MBI-26 | Ciprofloxacin | Lowest FIC MBI-26 and Ciprofloxacin |
|---|---|---|---|---|
| 1 | ATCC 23055 | 128 | 0.5 | 0.51 |
| 2 | 23 | 32 | 0.5 | 0.75 |
| 3 | 27 | 64 | 0.5 | 0.75 |
| 4 | 28 | 16 | 8 | 0.53 |
| 5 | 8220 | 64 | 2 | 0.5 |
| 6 | 8221 | 64 | 1 | 0.5 |
| 7 | 8222 | 64 | 1 | 0.5 |
| 8 | 8223 | 64 | 2 | 0.38 |
| 9 | 8224 | 64 | 2 | 0.5 |
| 10 | 8225 | 64 | 2 | 0.38 |
| 11 | 8226 | 64 | 2 | 0.38 |

TABLE 9

Synergy of MBI-29 + Ciprofloxacin against *A. calcoaceticus*

| Isolate Number | Strain Number | MIC (μg · mL$^{-1}$) MBI-29 | Ciprofloxacin | Lowest FIC MBI-29 and Ciprofloxacin |
|---|---|---|---|---|
| 1 | ATCC 23055 | 32 | 0.5 | 0.51 |
| 2 | 23 | 32 | 0.5 | 0.75 |
| 3 | 27 | 32 | 8 | 0.63 |
| 4 | 28 | 32 | 8 | 0.63 |
| 5 | 8220 | 16 | 2 | 0.56 |
| 6 | 8221 | 16 | 0.5 | 1 |
| 7 | 8222 | 16 | 2 | 0.75 |
| 8 | 8223 | 16 | 2 | 0.75 |
| 9 | 8224 | 16 | 1 | 1 |
| 10 | 8225 | 16 | 2 | 0.75 |
| 11 | 8226 | 16 | 2 | 0.75 |

TABLE 10

Synergy of MBI-26 + Imipenem against *A. calcoaceticus*

| Isolate Number | Strain Number | MIC (µg · mL$^{-1}$) MBI-26 | MIC (µg · mL$^{-1}$) Imipenem | Lowest FIC MBI-26 and Imipenem |
|---|---|---|---|---|
| 1 | ATCC 23055 | 128 | 2 | 1.0 |
| 2 | 23 | 64 | 512 | 0.13 |
| 3 | 27 | 32 | 512 | 0.14 |
| 4 | 28 | 32 | 16 | 0.25 |
| 5 | 8220 | 32 | 2 | 0.53 |
| 6 | 8221 | 64 | 1 | 1.01 |
| 7 | 8222 | 64 | 4 | 0.31 |
| 8 | 8223 | 32 | 2 | 0.75 |
| 9 | 8224 | 64 | 2 | 0.63 |
| 10 | 8225 | 64 | 2 | 0.63 |
| 11 | 8226 | 64 | 4 | 0.5 |

TABLE 11

Synergy of MBI-29 + Imipenem against *A. calcoaceticus*

| Isolate Number | Strain Number | MIC (µg · mL$^{-1}$) MBI-29 | MIC (µg · mL$^{-1}$) Imipenem | Lowest FIC MBI-26 and Imipenem |
|---|---|---|---|---|
| 1 | ATCC 23055 | 64 | 2 | 1 |
| 2 | 23 | 32 | 512 | 0.13 |
| 3 | 27 | 8 | 512 | 0.5 |
| 4 | 28 | 32 | 8 | 0.5 |
| 5 | 8220 | 8 | 2 | 1 |
| 6 | 8221 | 8 | 1 | 1.03 |
| 7 | 8222 | 32 | 2 | 0.75 |
| 8 | 8223 | 16 | 2 | 1 |
| 9 | 8224 | 32 | 2 | 0.51 |
| 10 | 8225 | 32 | 2 | 0.51 |
| 11 | 8226 | 32 | 2 | 1 |

TABLE 12

Synergy of MBI-26 + Tobramycin against *A. calcoaceticus*

| Isolate Number | Strain Number | MIC (µg · mL$^{-1}$) MBI-26 | MIC (µg · mL$^{-1}$) Tobramycin | Lowest FIC MBI-26 and Tobramycin |
|---|---|---|---|---|
| 1 | ATCC 23055 | 64 | 4 | 0.31 |
| 2 | 23 | 32 | 16 | ND |
| 3 | 27 | 32 | 1 | 1.01 |
| 4 | 28 | 32 | 128 | 0.26 |
| 5 | 8220 | 64 | 4 | 0.5 |
| 6 | 8221 | 64 | 4 | 0.5 |
| 7 | 8222 | 64 | 4 | 0.5 |
| 8 | 8223 | 64 | 4 | 0.5 |
| 9 | 8224 | 64 | 4 | 0.5 |
| 10 | 8225 | 64 | 4 | 0.5 |
| 11 | 8226 | 64 | 4 | 0.5 |

TABLE 13

Synergy of MBI-29 + Tobramycin against *A. calcoaceticus*

| Isolate Number | Strain Number | MIC (µg · mL$^{-1}$) MBI-29 | MIC (µg · mL$^{-1}$) Tobramycin | Lowest FIC MBI-29 and Tobramycin |
|---|---|---|---|---|
| 1 | ATCC 23055 | 32 | 2 | 0.75 |
| 2 | 23 | 4 | 4 | 1.25 |
| 3 | 27 | 8 | 1 | 1.03 |
| 4 | 28 | 32 | 128 | 0.26 |
| 5 | 8220 | 32 | 4 | 0.5 |
| 6 | 8221 | 32 | 4 | 0.5 |
| 7 | 8222 | 32 | 4 | 0.5 |
| 8 | 8223 | 32 | 4 | 0.5 |
| 9 | 8224 | 32 | 4 | 0.5 |
| 10 | 8225 | 32 | 4 | 0.5 |
| 11 | 8226 | 32 | 4 | 0.5 |

TABLE 14

Synergy of MBI-26 + Piperacillin against *A. calcoaceticus*

| Isolate Number | Strain Number | MIC (µg · mL$^{-1}$) MBI-26 | MIC (µg · mL$^{-1}$) Piperacillin | Lowest FIC MBI-26 and Piperacillin |
|---|---|---|---|---|
| 1 | ATCC 23055 | 64 | 8 | 0.75 |
| 2 | 23 | 32 | 1024 | 0.26 |
| 3 | 27 | 32 | 16 | 0.38 |
| 4 | 28 | 16 | 4 | 1.03 |
| 5 | 8220 | 64 | 16 | 0.38 |
| 6 | 8221 | 64 | 16 | 0.38 |
| 7 | 8222 | 64 | 32 | 0.25 |
| 8 | 8223 | 64 | 128 | 0.13 |
| 9 | 8224 | 64 | 256 | 0.16 |
| 10 | 8225 | 64 | 32 | 0.25 |
| 11 | 8226 | 64 | 32 | 0.25 |

TABLE 15

Synergy of MBI-29 + Piperacillin against *A. calcoaceticus*

| Isolate Number | Strain Number | MIC (µg · mL$^{-1}$) MBI-29 | MIC (µg · mL$^{-1}$) Piperacillin | Lowest FIC MBI-29 and Piperacillin |
|---|---|---|---|---|
| 1 | ATCC 23055 | 32 | 8 | 1 |
| 2 | 23 | 16 | 1024 | 0.28 |
| 3 | 27 | 16 | 16 | 0.5 |
| 4 | 28 | 8 | 4 | 1.03 |
| 5 | 8220 | 32 | 16 | 0.5 |
| 6 | 8221 | 32 | 16 | 0.38 |
| 7 | 8222 | 32 | 32 | 0.25 |
| 8 | 8223 | 32 | 32 | 0.25 |
| 9 | 8224 | 32 | 128 | 0.19 |
| 10 | 8225 | 32 | 32 | 0.25 |
| 11 | 8226 | 32 | 32 | 0.25 |

TABLE 16

Synergy of MBI-26 + Ceftazidime against *A. calcoaceticus*

| Isolate Number | Strain Number | MIC (µg · mL$^{-1}$) MBI-26 | MIC (µg · mL$^{-1}$) Ceftazidime | Lowest FIC MBI-26 and Ceftazidime |
|---|---|---|---|---|
| 1 | ATCC 23055 | 128 | 2 | 1.01 |
| 2 | 23 | 64 | 128 | 0.25 |
| 3 | 27 | 32 | 32 | 0.38 |
| 4 | 28 | 32 | 16 | 0.38 |

TABLE 16-continued

Synergy of MBI-26 + Ceftazidime against *A. calcoaceticus*

| Isolate Number | Strain Number | MIC (µg · mL⁻¹) MBI-26 | Ceftazidime | Lowest FIC MBI-26 and Ceftazidime |
|---|---|---|---|---|
| 5 | 8220 | 32 | 16 | 0.38 |
| 6 | 8221 | 64 | 8 | 0.25 |
| 7 | 8222 | 64 | 16 | 0.5 |
| 8 | 8223 | 32 | 16 | 0.25 |
| 9 | 8224 | 64 | 64 | 0.25 |
| 10 | 8225 | 64 | 32 | 0.31 |
| 11 | 8226 | 64 | 64 | 0.38 |

TABLE 17

Synergy of MBI-29 + Ceftazidime against *A. calcoaceticus*

| Isolate Number | Strain Number | MIC (µg · mL⁻¹) MBI-29 | Ceftaidime | Lowest FIC MBI-29 and Ceftazidime |
|---|---|---|---|---|
| 1 | ATCC 23055 | 64 | 4 | 0.63 |
| 2 | 23 | 32 | 128 | 0.26 |
| 3 | 27 | 8 | 4 | 1.5 |
| 4 | 28 | 32 | 16 | 0.63 |
| 5 | 8220 | 8 | 8 | 1.03 |
| 6 | 8221 | 16 | 8 | 1 |
| 7 | 8222 | 32 | 16 | 0.38 |
| 8 | 8223 | 16 | 16 | 0.75 |
| 9 | 8224 | 32 | 64 | 0.25 |
| 10 | 8225 | 32 | 8 | 0.5 |
| 11 | 8226 | 32 | 16 | 0.38 |

TABLE 18

Synergy of MBI-26 + Ciprofloxacin against *E. cloacae*

| Isolate Number | Strain Number | MIC (µg · mL⁻¹) MBI-26 | Ciprofloxacin | Lowest FIC MBI-26 and Ciprofloxacin |
|---|---|---|---|---|
| 12 | ATCC 13047 | 64 | 0.25 | 1.01 |
| 13 | 37-1 | 256 | 1 | 0.26 |
| 14 | 938-2 | 64 | 1 | 0.31 |
| 15 | B5546 | 64 | 1 | 0.38 |
| 16 | R4148 | 64 | 2 | 0.38 |
| 17 | R4148-2 | 64 | 2 | 0.38 |
| 18 | 3077 | 64 | 0.5 | 0.75 |
| 19 | 3356 | 128 | 0.25 | 1 |
| 20 | 14269 | 256 | 1 | 0.28 |
| 21 | 14661 | 512 | 1 | 0.28 |
| 22 | 18801 | 32 | 1 | 0.38 |

TABLE 19

Synergy of MBI-29 + Ciprofloxacin against *E. cloacae*

| Isolate Number | Strain Number | MIC (µg · mL⁻¹) MBI-29 | Ciprofloxacin | Lowest FIC MBI-29 and Ciprofloxacin |
|---|---|---|---|---|
| 12 | ATCC 13047 | 32 | 0.25 | 1.01 |
| 13 | 37-1 | 32 | 1 | 1 |
| 14 | 938-2 | 32 | 1 | 0.5 |
| 15 | B5546 | 32 | 1 | 0.5 |
| 16 | R4148 | 32 | 2 | 0.63 |
| 17 | R4148-2 | 16 | 2 | 0.75 |
| 18 | 3077 | 32 | 1 | 0.75 |
| 19 | 3356 | 32 | 0.25 | 1.01 |
| 20 | 14269 | 32 | 1 | 0.75 |
| 21 | 14661 | 32 | 1 | 0.75 |
| 22 | 18801 | 32 | 1 | 0.75 |

TABLE 20

Synergy of MBI-26 + Imipenem against *E. cloacae*

| Isolate Number | Strain Number | MIC (µg · mL⁻¹) MBI-26 | Imipenem | Lowest FIC MBI-26 and Imipenem |
|---|---|---|---|---|
| 12 | ATCC 13047 | 16 | 1 | 1 |
| 13 | 37-1 | 64 | 2 | 0.75 |
| 14 | 938-2 | 64 | 4 | 0.75 |
| 15 | B5546 | 64 | 2 | 1 |
| 16 | R4148 | 64 | 4 | 0.75 |
| 17 | R4148-2 | 32 | 2 | 1 |
| 18 | 3077 | 64 | 4 | 0.75 |
| 19 | 3356 | 64 | 4 | 0.75 |
| 20 | 14269 | 64 | 4 | 0.51 |
| 21 | 14661 | 64 | 2 | 1.01 |
| 22 | 18801 | 64 | 2 | 1.01 |

TABLE 21

Synergy of MBI-29 + Imipenem against *E. cloacae*

| Isolate Number | Strain Number | MIC (µg · mL⁻¹) MBI-29 | Imipenem | Lowest FIC MBI-29 and Imipenem |
|---|---|---|---|---|
| 12 | ATCC 13047 | 64 | 2 | 1 |
| 13 | 37-1 | 128 | 2 | 1 |
| 14 | 938-2 | 32 | 2 | 1.5 |
| 15 | B5546 | 32 | 2 | 0.75 |
| 16 | R4148 | 64 | 4 | 0.56 |
| 17 | R4148-2 | 32 | 2 | 0.75 |
| 18 | 3077 | 32 | 2 | 1 |
| 19 | 3356 | 32 | 2 | 1.5 |
| 20 | 14269 | 128 | 2 | 1 |
| 21 | 14661 | 64 | 2 | 1 |
| 22 | 18801 | 64 | 2 | 1 |

TABLE 22

Synergy of MBI-26 + Tobramycin against *E. cloacae*

| Isolate Number | Strain Number | MIC (µg · mL⁻¹) MBI-26 | Tobramycin | Lowest FIC MBI-26 and Tobramycin |
|---|---|---|---|---|
| 12 | ATCC 13047 | 64 | 1 | 1.01 |
| 13 | 37-1 | 64 | 1 | 1.01 |
| 14 | 938-2 | 64 | 2 | 1.01 |
| 15 | B5546 | 32 | 2 | 0.51 |
| 16 | R4148 | 32 | 1 | 1.06 |
| 17 | R4148-2 | 64 | 1 | ND |
| 18 | 3077 | 64 | 1 | 1.06 |
| 19 | 3356 | 64 | 1 | 1.01 |

TABLE 22-continued

Synergy of MBI-26 + Tobramycin against E. cloacae

| Isolate Number | Strain Number | MIC ($\mu g \cdot mL^{-1}$) MBI-26 | Tobramycin | Lowest FIC MBI-26 and Tobramycin |
|---|---|---|---|---|
| 20 | 14269 | 64 | 1 | 1.01 |
| 21 | 14661 | 64 | 1 | 1.01 |
| 22 | 18801 | 32 | 1 | 1.01 |

TABLE 23

Synergy of MBI-29 + Tobramycin against E. cloacae

| Isolate Number | Strain Number | MIC ($\mu g \cdot mL^{-1}$) MBI-29 | Tobramycin | Lowest FIC MBI-29 and Tobramycin |
|---|---|---|---|---|
| 12 | ATCC 13047 | 32 | 1 | 1 |
| 13 | 37-1 | 32 | 1 | 1 |
| 14 | 938-2 | 16 | 1 | 1.01 |
| 15 | B5546 | 32 | 1 | 1.01 |
| 16 | R4148 | 16 | 1 | 1.03 |
| 17 | R4148-2 | 16 | 1 | 1.01 |
| 18 | 3077 | 32 | 1 | 1.01 |
| 19 | 3356 | 32 | 1 | 1.01 |
| 20 | 14269 | 16 | 1 | 1.01 |
| 21 | 14661 | 32 | 1 | 1.01 |
| 22 | 18801 | 16 | 1 | 1.01 |

TABLE 24

Synergy of MBI-26 + Piperacillin against E. cloacae

| Isolate Number | Strain Number | MIC ($\mu g \cdot mL^{-1}$) MBI-26 | Piperacillin | Lowest FIC MBI-26 and Piperacillin |
|---|---|---|---|---|
| 12 | ATCC 13047 | 64 | 8 | 0.75 |
| 13 | 37-1 | 64 | 4 | 1.01 |
| 14 | 938-2 | 64 | 8 | 0.51 |
| 15 | B5546 | 64 | 8 | 0.56 |
| 16 | R4148 | 64 | 1024 | 0.13 |
| 17 | R4148-2 | 64 | 1024 | 0.25 |
| 18 | 3077 | 64 | 8 | 0.56 |
| 19 | 3356 | 64 | 64 | 0.25 |
| 20 | 14269 | 512 | 1024 | 0.03 |
| 21 | 14661 | 64 | 16 | 0.5 |
| 22 | 18801 | 32 | 4 | 1.01 |

TABLE 25

Synergy of MBI-29 + Piperacillin against E. cloacae

| Isolate Number | Strain Number | MIC ($\mu g \cdot mL^{-1}$) MBI-29 | Piperacillin | Lowest FIC MBI-29 and Piperacillin |
|---|---|---|---|---|
| 12 | ATCC 13047 | 32 | 8 | 0.75 |
| 13 | 37-1 | 32 | 4 | 1.01 |
| 14 | 938-2 | 32 | 4 | 1.01 |
| 15 | B5546 | 32 | 8 | 0.63 |
| 16 | R4148 | 32 | 1024 | 0.28 |
| 17 | R4148-2 | 32 | 1024 | 0.28 |
| 18 | 3077 | 32 | 4 | 1.01 |
| 19 | 3356 | 32 | 64 | 0.31 |

TABLE 25-continued

Synergy of MBI-29 + Piperacillin against E. cloacae

| Isolate Number | Strain Number | MIC ($\mu g \cdot mL^{-1}$) MBI-29 | Piperacillin | Lowest FIC MBI-29 and Piperacillin |
|---|---|---|---|---|
| 20 | 14269 | 128 | 1024 | 0.07 |
| 21 | 14661 | 32 | 8 | 1.01 |
| 22 | 18801 | 16 | 4 | 1.01 |

TABLE 26

Synergy of MBI-26 + Ceftazidime against E. cloacae

| Isolate Number | Strain Number | MIC ($\mu g \cdot mL^{-1}$) MBI-26 | Ceftazidime | Lowest FIC MBI-26 and Ceftazidime |
|---|---|---|---|---|
| 12 | ATCC 13047 | 16 | 4 | 0.75 |
| 13 | 37-1 | 256 | 2 | 1 |
| 14 | 938-2 | 64 | 2 | 1.01 |
| 15 | B5546 | 64 | 2 | 1.01 |
| 16 | R4148 | 64 | 512 | 0.25 |
| 17 | R4148-2 | 32 | 512 | 31 |
| 18 | 3077 | 64 | 2 | 1.01 |
| 19 | 3356 | 128 | 128 | 0.19 |
| 20 | 14269 | 512 | 512 | 0.03 |
| 21 | 14661 | 512 | 512 | 0.03 |
| 22 | 18801 | 256 | 2 | 1 |

TABLE 27

Synergy of MBI-29 + Ceftazidime against E. cloacae

| Isolate Number | Strain Number | MIC ($\mu g \cdot mL^{-1}$) MBI-29 | Ceftazidime | Lowest FIC MBI-29 and Ceftazidime |
|---|---|---|---|---|
| 12 | ATCC 13047 | 64 | 4 | 0.53 |
| 13 | 37-1 | 128 | 2 | 1 |
| 14 | 938-2 | 32 | 2 | 1.01 |
| 15 | B5546 | 32 | 2 | 1.01 |
| 16 | R4148 | 64 | 512 | 0.16 |
| 17 | R4148-2 | 32 | 512 | 0.28 |
| 18 | 3077 | 32 | 2 | 1.01 |
| 19 | 3356 | 32 | 128 | 0.3 |
| 20 | 14269 | 128 | 512 | 0.09 |
| 21 | 14661 | 128 | 512 | 0.09 |
| 22 | 18801 | 128 | 2 | 1 |

TABLE 28

Synergy of MBI-26 + Ciprofloxacin against P. aeruginosa

| Isolate Number | Strain Number | MIC ($\mu g \cdot mL^{-1}$) MBI-26 | Ciprofloxacin | Lowest FIC MBI-26 and Ciprofloxacin |
|---|---|---|---|---|
| 23 | ATCC 27853 | 64 | 1 | 0.56 |
| 24 | 34 | 64 | 1 | 0.53 |
| 25 | 923-1 | 64 | 0.25 | 1.01 |
| 26 | 3101 | 64 | 0.25 | 1.01 |
| 27 | 14644 | 256 | 32 | ND |
| 28 | 15036 | 256 | 16 | 1 |
| 29 | 15545 | 64 | 0.25 | 1.01 |
| 30 | B3999-1 | 64 | 0.25 | 1.01 |
| 31 | U7688-1 | 64 | 0.25 | 1.01 |

TABLE 28-continued

Synergy of MBI-26 + Ciprofloxacin against P. aeruginosa

| | | MIC ($\mu g \cdot mL^{-1}$) | | Lowest FIC MBI-26 and |
|---|---|---|---|---|
| Isolate Number | Strain Number | MBI-26 | Cipro-floxacin | Cipro-floxacin |
| 32 | W2897-1 | 64 | 0.25 | 1.01 |
| 33 | W5483-2 | 64 | 0.25 | 1.01 |

TABLE 29

Synergy of MBI-29 + Ciprofloxacin against P. aeruginosa

| | | MIC ($\mu g \cdot mL^{-1}$) | | Lowest FIC MBI-29 and |
|---|---|---|---|---|
| Isolate Number | Strain Number | MBI-29 | Cipro-floxacin | Cipro-floxacin |
| 23 | ATCC 27853 | 32 | 1 | 0.56 |
| 24 | 34 | 32 | 1 | 0.75 |
| 25 | 923-1 | 32 | 0.25 | 1.01 |
| 26 | 3101 | 32 | 0.25 | 1.01 |
| 27 | 14644 | 128 | 32 | ND |
| 28 | 15036 | 128 | 32 | ND |
| 29 | 15545 | 32 | 0.25 | 0.63 |
| 30 | B3999-1 | 32 | 0.25 | 1.01 |
| 31 | U7688-1 | 32 | 0.25 | 1.01 |
| 32 | W2897-1 | 32 | 0.25 | 1.01 |
| 33 | W5483-2 | 32 | 0.25 | 1.01 |

TABLE 30

Synergy of MBI-26 + Imipenem against P. aeruginosa

| | | MIC ($\mu g \cdot mL^{-1}$) | | Lowest FIC MBI-26 and |
|---|---|---|---|---|
| Isolate Number | Strain Number | MBI-26 | Imipenem | Imipenem |
| 23 | ATCC 27853 | 64 | 8 | 0.5 |
| 24 | 34 | 128 | 512 | 0.38 |
| 25 | 923-1 | 64 | 4 | 1.01 |
| 26 | 3101 | 64 | 8 | 0.75 |
| 27 | 14644 | 64 | 16 | 0.51 |
| 28 | 15036 | 64 | 16 | 1 |
| 29 | 15545 | 64 | 128 | ND |
| 30 | B3999-1 | 64 | 128 | ND |
| 31 | U7688-1 | 64 | 16 | 1 |
| 32 | W2897-1 | 64 | 128 | 0.25 |
| 33 | W5483-2 | 64 | 64 | ND |

TABLE 31

Synergy of MBI-29 + Imipenem against P. aeruginosa

| | | MIC ($\mu g \cdot mL^{-1}$) | | Lowest FIC MBI-29 and |
|---|---|---|---|---|
| Isolate Number | Strain Number | MBI-29 | Imipenem | Imipenem |
| 23 | ATCC 27853 | 64 | 4 | 0.75 |
| 24 | 34 | 32 | 512 | 0.16 |
| 25 | 923-1 | 64 | 2 | 1.13 |
| 26 | 3101 | 32 | 4 | 0.75 |
| 27 | 14644 | 64 | 8 | 1 |
| 28 | 15036 | 64 | 8 | 1 |
| 29 | 15545 | 32 | 256 | 0.63 |
| 30 | B3999-1 | 64 | 256 | 1 |
| 31 | U7688-1 | 64 | 256 | 0.75 |

TABLE 31-continued

Synergy of MBI-29 + Imipenem against P. aeruginosa

| | | MIC ($\mu g \cdot mL^{-1}$) | | Lowest FIC MBI-29 and |
|---|---|---|---|---|
| Isolate Number | Strain Number | MBI-29 | Imipenem | Imipenem |
| 32 | W2897-1 | 32 | 256 | 0.75 |
| 33 | W5483-2 | 64 | 256 | 0.5 |

TABLE 32

Synergy of MBI-26 + Tobramycin against P. aeruginosa

| | | MIC ($\mu g \cdot mL^{-1}$) | | Lowest FIC MBI-29 and |
|---|---|---|---|---|
| Isolate Number | Strain Number | MBI-26 | Tobramycin | Tobramycin |
| 23 | ATCC 27853 | 64 | 1 | 1.01 |
| 24 | 34 | 128 | 128 | 0.5 |
| 25 | 923-1 | 64 | 1 | 1.01 |
| 26 | 3101 | 64 | 1 | 1.01 |
| 27 | 14644 | 64 | 2 | 0.53 |
| 28 | 15036 | 64 | 1 | 1.01 |
| 29 | 15545 | 64 | 2 | 1 |
| 30 | B3999-1 | 64 | 2 | 0.51 |
| 31 | U7688-1 | 64 | 1 | 1.01 |
| 32 | W2897-1 | 64 | 1 | 1.01 |
| 33 | W5483-2 | 64 | 1 | 1.01 |

TABLE 33

Synergy of MBI-29 + Tobramycin against P. aeruginosa

| | | MIC ($\mu g \cdot mL^{-1}$) | | Lowest FIC MBI-29 and |
|---|---|---|---|---|
| Isolate Number | Strain Number | MBI-29 | Tobramycin | Tobramycin |
| 23 | ATCC 27853 | 32 | 1 | 1.01 |
| 24 | 34 | 16 | 64 | 0.5 |
| 25 | 923-1 | 32 | 1 | 1.01 |
| 26 | 3101 | 32 | 1 | 1.01 |
| 27 | 14644 | 32 | 1 | 1.01 |
| 28 | 15036 | 32 | 1 | 1.01 |
| 29 | 15545 | 32 | 2 | 0.75 |
| 30 | B3999-1 | 32 | 1 | 1.01 |
| 31 | U7688-1 | 32 | 2 | 0.56 |
| 32 | W2897-1 | 32 | 1 | 1.01 |
| 33 | W5483-2 | 32 | 2 | 0.51 |

TABLE 34

Synergy of MBI-26 + Piperacillin against P. aeruginosa

| | | MIC ($\mu g \cdot mL^{-1}$) | | Lowest FIC MBI-26 and |
|---|---|---|---|---|
| Isolate Number | Strain Number | MBI-26 | Piperacillin | Piperacillin |
| 23 | ATCC 27853 | 128 | 256 | 0.19 |
| 24 | 34 | 128 | 1024 | 0.5 |
| 25 | 923-1 | 64 | 64 | 0.5 |
| 26 | 3101 | 64 | 64 | 0.63 |
| 27 | 14644 | 64 | 512 | ND |
| 28 | 15036 | 256 | 1024 | 0.09 |
| 29 | 15545 | 256 | 512 | 0.14 |
| 30 | B3999-1 | 256 | 512 | 0.25 |

TABLE 34-continued

Synergy of MBI-26 + Piperacillin against *P. aeruginosa*

| Isolate Number | Strain Number | MIC (µg · mL⁻¹) MBI-26 | Piperacillin | Lowest FIC MBI-26 and Piperacillin |
|---|---|---|---|---|
| 31 | U7688-1 | 256 | 512 | ND |
| 32 | W2897-1 | 64 | 64 | 1 |
| 33 | W5483-2 | 256 | 128 | 1 |

TABLE 35

Synergy of MBI-29 + Piperacillin against *P. aeruginosa*

| Isolate Number | Strain Number | MIC (µg · mL⁻¹) MBI-29 | Piperacillin | Lowest FIC MBI-29 and Piperacillin |
|---|---|---|---|---|
| 23 | ATCC 27853 | 64 | 128 | ND |
| 24 | 34 | 32 | 1024 | 0.28 |
| 25 | 923-1 | 32 | 32 | 0.5 |
| 26 | 3101 | 32 | 128 | 0.31 |
| 27 | 14644 | 128 | 1024 | ND |
| 28 | 15036 | 128 | 1024 | 0.09 |
| 29 | 15545 | 64 | 512 | 0.16 |
| 30 | B3999-1 | 128 | 256 | 0.12 |
| 31 | U7688-1 | 32 | 256 | 0.5 |
| 32 | W2897-1 | 32 | 32 | 0.75 |
| 33 | W5483-2 | 128 | 512 | 0.19 |

TABLE 36

Synergy of MBI-26 + Ceftazidime against *P. aeruginosa*

| Isolate Number | Strain Number | MIC (µg · mL⁻¹) MBI-26 | Ceftazidime | Lowest FIC MBI-29 and Ceftazidime |
|---|---|---|---|---|
| 23 | ATCC 27853 | 128 | 32 | 0.31 |
| 24 | 34 | 128 | 32 | 0.75 |
| 25 | 923-1 | 128 | 4 | 1.01 |
| 26 | 3101 | 128 | 8 | 0.56 |
| 27 | 14644 | 256 | 128 | 1 |
| 28 | 15036 | 256 | 2 | 2 |
| 29 | 15545 | 256 | 8 | 0.53 |
| 30 | B3999-1 | 256 | 16 | 1.01 |
| 31 | U7688-1 | 256 | 32 | 0.25 |
| 32 | W2897-1 | 256 | 32 | 0.26 |
| 33 | W5483-2 | 256 | 8 | 1.01 |

TABLE 37

Synergy of MBI-29 + Ceftazidime against *P. aeruginosa*

| Isolate Number | Strain Number | MIC (µg · mL⁻¹) MBI-29 | Ceftazidime | Lowest FIC MBI-29 and Ceftazidime |
|---|---|---|---|---|
| 23 | ATCC 27853 | 64 | 32 | 0.38 |
| 24 | 34 | 32 | 64 | 0.31 |
| 25 | 923-1 | 64 | 4 | 0.56 |
| 26 | 3101 | 64 | 8 | 0.56 |
| 27 | 14644 | 128 | 256 | 1 |
| 28 | 15036 | 128 | 4 | 0.51 |
| 29 | 15545 | 64 | 8 | 0.5 |
| 30 | B3999-1 | 128 | 8 | 0.31 |

TABLE 37-continued

Synergy of MBI-29 + Ceftazidime against *P. aeruginosa*

| Isolate Number | Strain Number | MIC (µg · mL⁻¹) MBI-29 | Ceftazidime | Lowest FIC MBI-29 and Ceftazidime |
|---|---|---|---|---|
| 31 | U7688-1 | 128 | 8 | 0.63 |
| 32 | W2897-1 | 64 | 4 | 0.51 |
| 33 | W5483-2 | 128 | 8 | 0.56 |

TABLE 38

Synergy of MBI-26 + Ciprofloxacin against *X. maltophila*

| Isolate Number | Strain Number | MIC (µg · mL⁻¹) MBI-26 | Ciprofloxacin | Lowest FIC MBI-26 and Ciprofloxacin |
|---|---|---|---|---|
| 34 | ATCC 13637 | 64 | 0.5 | 0.63 |
| 35 | 6 | 64 | 4 | 0.38 |
| 36 | 16 | 64 | 8 | 1 |
| 37 | 3095 | 64 | 16 | 1 |
| 38 | 7901 | 256 | 32 | ND |
| 39 | B3110.1 | 64 | 2 | 2.01 |
| 40 | R1302-1 | 128 | 4 | 1 |
| 41 | R4230 | 64 | 2 | 1 |
| 42 | TF29-1 | 128 | 8 | ND |
| 43 | TF29-2 | 128 | 8 | 1 |
| 44 | W6896-2 | 256 | 4 | 0.13 |
| 45 | W11291 | 64 | 2 | 2.01 |

TABLE 39

Synergy of MBI-29 + Ciprofloxacin against *X. maltophila*

| Isolate Number | Strain Number | MIC (µg · mL⁻¹) MBI-29 | Ciprofloxacin | Lowest FIC MBI-29 and Ciprofloxacin |
|---|---|---|---|---|
| 34 | ATCC 13637 | 32 | 0.5 | 1.01 |
| 35 | 6 | 32 | 2 | 0.38 |
| 36 | 16 | 32 | 8 | ND |
| 37 | 3095 | 64 | 16 | 0.5 |
| 38 | 7901 | 64 | 32 | 0.75 |
| 39 | B3110.1 | 32 | 2 | 1.01 |
| 40 | R1302-1 | 32 | 4 | 0.56 |
| 41 | R4230 | 16 | 4 | 0.5 |
| 42 | TF29-1 | 16 | 8 | 1 |
| 43 | TF29-2 | 16 | 8 | 0.53 |
| 44 | W6896-2 | 16 | 8 | 1 |
| 45 | W11291 | 32 | 4 | 0.75 |

TABLE 40

Synergy of MBI-26 + Imipenem against *X. maltophila*

| Isolate Number | Strain Number | MIC (µg · mL⁻¹) MBI-29 | Imipenem | Lowest FIC MBI-26 and Imipenem |
|---|---|---|---|---|
| 34 | ATCC 13637 | 64 | 512 | 0.13 |
| 35 | 6 | 128 | 512 | 0.16 |
| 36 | 16 | 256 | 512 | ND |
| 37 | 3095 | 512 | 512 | ND |
| 38 | 7901 | 256 | 512 | ND |
| 39 | B3110.1 | 256 | 512 | ND |
| 40 | R1302-1 | 128 | 512 | ND |
| 41 | R4230 | 64 | 512 | ND |

TABLE 40-continued

Synergy of MBI-26 + Imipenem against *X. maltophila*

| Isolate Number | Strain Number | MIC (µg · mL$^{-1}$) MBI-29 | MIC (µg · mL$^{-1}$) Imipenem | Lowest FIC MBI-26 and Imipenem |
|---|---|---|---|---|
| 42 | TF29-1 | 128 | 512 | ND |
| 43 | TF29-2 | 128 | 512 | ND |
| 44 | W6896-2 | 256 | 512 | 0.25 |
| 45 | W11291 | 512 | 512 | ND |

TABLE 41

Synergy of MBI-29 + Imipenem against *X. maltophila*

| Isolate Number | Strain Number | MIC (µg · mL$^{-1}$) MBI-29 | MIC (µg · mL$^{-1}$) Imipenem | Lowest FIC MBI-29 and Imipenem |
|---|---|---|---|---|
| 34 | ATCC 13637 | 32 | 512 | 0.19 |
| 35 | 6 | 32 | 512 | 0.25 |
| 36 | 16 | 32 | 512 | 0.3 |
| 37 | 3095 | 64 | 512 | ND |
| 38 | 7901 | 64 | 512 | 0.38 |
| 39 | B3110.1 | 32 | 512 | ND |
| 40 | R1302-1 | 64 | 512 | 0.25 |
| 41 | R4230 | 32 | 512 | 0.5 |
| 42 | TF29-1 | 16 | 512 | 0.56 |
| 43 | TF29-2 | 16 | 512 | 0.56 |
| 44 | W6896-2 | 64 | 512 | 0.38 |
| 45 | W11291 | 64 | 512 | 0.38 |

TABLE 42

Synergy of MBI-26 + Tobramycin against *X. maltophila*

| Isolate Number | Strain Number | MIC (µg · mL$^{-1}$) MBI-26 | MIC (µg · mL$^{-1}$) Tobramycin | Lowest FIC MBI-26 and Tobramycin |
|---|---|---|---|---|
| 34 | ATCC 13637 | 64 | 32 | 0.16 |
| 35 | 6 | 64 | 4 | 0.25 |
| 36 | 16 | 256 | 128 | 0.63 |
| 37 | 3095 | 32 | 32 | 0.5 |
| 38 | 7901 | 32 | 32 | 1.01 |
| 39 | B3110.1 | 256 | 32 | 0.63 |
| 40 | R1302-1 | 128 | 32 | 0.63 |
| 41 | R4230 | 64 | 16 | 0.38 |
| 42 | TF29-1 | 32 | 2 | 1.01 |
| 43 | TF29-2 | 32 | 2 | 1.01 |
| 44 | W6896-2 | 32 | 16 | 0.5 |
| 45 | W11291 | 512 | 128 | ND |

TABLE 43

Synergy of MBI-29 + Tobramycin against *X. maltophila*

| Isolate Number | Strain Number | MIC (µg · mL$^{-1}$) MBI-29 | MIC (µg · mL$^{-1}$) Tobramycin | Lowest FIC MBI-29 and Tobramycin |
|---|---|---|---|---|
| 34 | ATCC 13637 | 8 | 8 | 0.63 |
| 35 | 6 | 16 | 4 | 0.75 |
| 36 | 16 | 32 | 128 | 0.31 |
| 37 | 3095 | 64 | 32 | 0.16 |
| 38 | 7901 | 64 | 32 | 0.28 |
| 39 | B3110.1 | 32 | 16 | 0.56 |
| 40 | R1302-1 | 64 | 32 | 0.53 |

TABLE 43-continued

Synergy of MBI-29 + Tobramycin against *X. maltophila*

| Isolate Number | Strain Number | MIC (µg · mL$^{-1}$) MBI-29 | MIC (µg · mL$^{-1}$) Tobramycin | Lowest FIC MBI-29 and Tobramycin |
|---|---|---|---|---|
| 41 | R4230 | 16 | 16 | 0.56 |
| 42 | TF29-1 | 8 | 1 | 1.03 |
| 43 | TF29-2 | 16 | 1 | 1.5 |
| 44 | W6896-2 | 16 | 8 | 0.63 |
| 45 | W11291 | 64 | 128 | ND |

TABLE 44

Synergy of MBI-26 + Piperacillin against *X. maltophila*

| Isolate Number | Strain Number | MIC (µg · mL$^{-1}$) MBI-26 | MIC (µg · mL$^{-1}$) Piperacillin | Lowest FIC MBI-26 and Piperacillin |
|---|---|---|---|---|
| 34 | ATCC 13637 | 64 | 1024 | 0.14 |
| 35 | 6 | 64 | 512 | ND |
| 36 | 16 | 256 | 1024 | ND |
| 37 | 3095 | 64 | 512 | ND |
| 38 | 7901 | 64 | 512 | ND |
| 39 | B3110.1 | 64 | 512 | ND |
| 40 | R1302-1 | 64 | 512 | ND |
| 41 | R4230 | 64 | 1024 | 0.5 |
| 42 | TF29-1 | 128 | 1024 | 0.2 |
| 43 | TF29-2 | 128 | 1024 | 0.5 |
| 44 | W6896-2 | 32 | 1024 | 0.6 |
| 45 | W11291 | 64 | 512 | ND |

TABLE 45

Synergy of MBI-29 + Piperacillin against *X. maltophila*

| Isolate Number | Strain Number | MIC (µg · mL$^{-1}$) MBI-26 | MIC (µg · mL$^{-1}$) Piperacillin | Lowest FIC MBI-29 and Piperacillin |
|---|---|---|---|---|
| 34 | ATCC 13637 | 32 | 1024 | 0.19 |
| 35 | 6 | 32 | 64 | 0.19 |
| 36 | 16 | 32 | 1024 | 0.38 |
| 37 | 3095 | 64 | 1024 | 0.38 |
| 38 | 7901 | 64 | 1024 | 0.28 |
| 39 | B3110.1 | 32 | 1024 | 0.63 |
| 40 | R1302-1 | 64 | 1024 | 0.25 |
| 41 | R4230 | 32 | 1024 | 0.3 |
| 42 | TF29-1 | 32 | 1024 | 0.2 |
| 43 | TF29-2 | 32 | 1024 | 0.28 |
| 44 | W6896-2 | 64 | 1024 | 0.13 |
| 45 | W11291 | 64 | 1024 | 0.31 |

TABLE 46

Synergy of MBI-26 + Ceftazidime against *X. maltophila*

| Isolate Number | Strain Number | MIC (µg · mL$^{-1}$) MBI-26 | MIC (µg · mL$^{-1}$) Ceftazidime | Lowest FIC MBI-26 and Ceftazidime |
|---|---|---|---|---|
| 34 | ATCC 13637 | 64 | 64 | 0.28 |
| 35 | 6 | 128 | 64 | 0.25 |
| 36 | 16 | 256 | 32 | 0.51 |
| 37 | 3095 | 512 | 512 | ND |
| 38 | 7901 | 256 | 128 | 1 |
| 39 | B3110.1 | 256 | 64 | 1.13 |

TABLE 46-continued

Synergy of MBI-26 + Ceftazidime against *X. maltophila*

| Isolate Number | Strain Number | MIC (µg · mL⁻¹) MBI-26 | MIC (µg · mL⁻¹) Ceftazidime | Lowest FIC MBI-26 and Ceftazidime |
|---|---|---|---|---|
| 40 | R1302-1 | 128 | 16 | 1 |
| 41 | R4230 | 64 | 4 | 1 |
| 42 | TF29-1 | 128 | 4 | 1 |
| 43 | TF29-2 | 128 | 4 | 1.01 |
| 44 | W6896-2 | 256 | 64 | 1 |
| 45 | W11291 | 512 | 128 | 1 |

TABLE 47

Synergy of MBI-29 + Ceftazidime against *X. maltophila*

| Isolate Number | Strain Number | MIC (µg · mL⁻¹) MBI-29 | MIC (µg · mL⁻¹) Ceftazidime | Lowest FIC MBI-29 and Ceftazidime |
|---|---|---|---|---|
| 34 | ATCC 13637 | 32 | 64 | 0.28 |
| 35 | 6 | 32 | 32 | 0.31 |
| 36 | 16 | 32 | 16 | 0.63 |
| 37 | 3095 | 64 | 512 | ND |
| 38 | 7901 | 64 | 256 | 0.31 |
| 39 | B3110.1 | 32 | 128 | 0.75 |
| 40 | R1302-1 | 64 | 32 | 0.25 |
| 41 | R4230 | 32 | 8 | 0.5 |
| 42 | TF29-1 | 16 | 4 | 1 |
| 43 | TF29-2 | 16 | 2 | 1.01 |
| 44 | W6896-2 | 64 | 64 | 0.5 |
| 45 | W11291 | 64 | 256 | 0.28 |

Note: MBI 26 (1.25 µg/mL) also showed synergy with Lysozyme (>64× reduction in MIC), Novobiocin (>4× reduction in MIC), Nalidixic acid (2× reduction in MIC) and carbenicillin (2× reduction in MIC).

Although the invention has been described with reference to the presently preferred embodiment, it should be understood that various modifications can be made without departing from the spirit of the invention. Accordingly, the invention is limited only by the following claims.

---

We claim:

1. An isolated peptide wherein the peptide has an amino acid sequence selected from the group consisting of:
NH2-KWKLFKKKGTGAVLTVLTTGLPALIS-COOH (SEQ ID NO: 11),
NH2-KKKSFIKLLTSAKVSVLTTAKPLISS-COOH (SEQ ID NO: 13),
NH2-KKWWRRVLSGLKTGPALSNV-COOH (SEQ ID NO: 15),
NH2-KKWWRRVLKGLSSGPALSNV-COOH (SEQ ID NO: 16),
NH$_2$-KKWWRRALQALKNGPALSNV-COOH (SEQ ID NO: 17),
NH2-KKWWRRVLSGLKTAGPAIQSVLNK-COOH (SEQ ID NO: 18),
NH2-KKWWRRALGLKTAGPAIQSVLNK-COOH (SEQ ID NO: 19),
NH2-KKWWKAQKAVNSGPNALQTLAQ-COOH (SEQ ID NO: 20),
NH2-KKWWKAKKFANSGPNALQTLAQ-COOH (SEQ ID NO: 21), and
NH2-KKWWKFIKKAVNSGTTGLQTLAS-COOH (SEQ ID NO:22).

2. A method of inhibiting the growth of bacteria comprising contacting the bacteria with an inhibiting effective amount of a peptide having an amino acid sequence selected from the group consisting of:
NH2-KWKSFIKKLTTAVKKVLTTGLPALIS-COOH (SEQ ID NO: 1),
NH2-KWKSFIKKLTSAAKKVVTFAKPLISS-COOH (SEQ ID NO: 2),
NH2-KWKSFIKNLITGGSKILTTGLPALTS-COOH (SEQ ID NO: 3),
NH2-KWKKFLTKGSKILTTGLPALIS-COOH (SEQ ID NO: 4),
NH2-KWKSFIKKLTSVLKKVVTTALPALIS-COOH (SEQ ID NO: 9),
NH2-KWKSFIKNLTKVLKKVVTTALPALIS-COOH (SEQ ID NO: 10),
NH2-KWKLFKKKGTGAVLTVLTTGLPALIS-COOH (SEQ ID NO: 11),
NH2-KWKSFIKKLTSVLKKVVITAKPLISS-COOH (SEQ ID NO: 12),
NH2-KKKSFIKLLTSAKVSVLTTAKPLISS-COOH (SEQ ID NO: 13),
NH2-KKWWRRVLSGLKTGPALSNV-COOH (SEQ ID NO: 15),
NH2-KKWWRRVLKGLSSGPALSNV-COOH (SEQ ID NO: 16),
NH$_2$-KKWWRRALQALKNGPALSNV-COOH (SEQ ID NO: 17),
NH2-KKWWRRVLSGLKTAGPAIQSVLNK-COOH (SEQ ID NO: 18),
NH2-KKWWRRALQGLKTAGPAIQSVLNK-COOH (SEQ ID NO: 19),
NH2-KKWWKAQKAVNSGPNALQTLAQ-COOH (SEQ ID NO: 20),
NH2-KKWWKAKKFANSGPNALQTLAQ-COOH (SEQ ID NO: 21), and
NH2-KKWWKFIKKAVNSGTTGLQTLAS-COOH (SEQ ID NO: 22).

3. The method of claim 2, wherein the bacteria is gram positive.

4. The method of claim 3, wherein bacteria is *Staphylococcus aureus* or *S. epidermidis*.

5. The method of claim 2, wherein the bacteria is gram negative.

6. The method of claim 5, wherein the bacteria is selected from the group consisting of *E. coli, P. aeruginosa*, and *S. typhimurium*.

7. The method of claim 2, wherein the peptide is administered in combination with at least one antibiotic.

8. The method of claim 7, wherein the class of antibiotic is selected from the group consisting of aminoglycosides, penicillins, cephalosporins, carbapenems, monobactams, quinolones, tetracyclines, glycopeptides, chloramphenicol, clindamycin, trimethoprim, sulfamethoxazole, nitrofuirantoin, rifampin and mupirocin.

9. The method of claim 8, wherein the antibiotic is selected from the group consisting of amikacin, gentamicin, kanamycin, netilmicin, t-obramycin, streptomycin, azithromycin, clarithromycin, erythromycin, erythromycin estolate/ethylsuccinate/gluceptatellactobionate/stearate, penicillin G, penicillin V, methicillin, nafcillin, oxacillin, cloxacillin, dicloxacillin, ampicillin, amoxicillin, ticarcillin, carbenicillin, mezlocillin, azlocillin, piperacillin, cephalothin, cefazolin, cefaclor, cefamandole, cefoxitin, cefuiroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, cefsulodin, i-mipenem, aztreonam, fleroxacin, nalidixic acid, norfloxacin, ciprofloxacin, ofloxacin, enoxacin, lomefloxacin, cinoxacin, doxycycline, m-inocycline, tetracycline, vancomycin, and teicoplanin.

10. An isolated peptide wherein the peptide has an amino acid sequence selected from the group consisting of
KKWWRR(V/A)L(S/K/Q)(G/A)L(K/S)(T/S/N)XGPA(I/L)X$_1$SX$_2$VX$_3$X$_2$X$_4$ (SEQ ID NO: 38); and
KKWWKX$_5$(A/I)(Q/K)K(A/F)(V/A)NSG(P/T)(N/T)(A/G)LQTLA(Q/S) (SEQ ID NO: 39),
wherein X is A or absent, X$_1$ is Q or absent, X$_2$ is N or absent, X$_3$ is L or absent, X$_4$ is K or absent and X$_5$ is F or absent.

* * * * *

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:1:

Lys Trp Lys Ser Phe Ile Lys Lys Leu Thr Thr Ala Val Lys Lys Val
 1               5                  10                  15

Leu Thr Thr Gly Leu Pro Ala Leu Ile Ser
            20                  25

(2) INFORMATION FOR SEQ ID NO:2:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:2:

Lys Trp Lys Ser Phe Ile Lys Lys Leu Thr Ser Ala Ala Lys Lys Val
 1               5                  10                  15

Val Thr Thr Ala Lys Pro Leu Ile Ser Ser
            20                  25

(2) INFORMATION FOR SEQ ID NO:3:

```
        (i) SEQUENCE CHARACTERISTICS:
            (A) LENGTH: 26 amino acids
            (B) TYPE: amino acid
            (D) TOPOLOGY: linear (ii) MOLECULE TYPE: peptide (xi) SEQUENCE DESCRIPTION: SEQ ID NO:3:

Lys Trp Lys Ser Phe Ile Lys Asn Leu Thr Lys Gly Gly Ser Lys Ile
 1               5                  10                  15

Leu Thr Thr Gly Leu Pro Ala Leu Ile Ser
                20                  25

(2) INFORMATION FOR SEQ ID NO:4:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (xi) SEQUENCE DESCRIPTION: SEQ ID NO:4:

Lys Trp Lys Lys Phe Ile Lys Asn Leu Thr Lys Gly Gly Ser Lys Ile
 1               5                  10                  15

Leu Thr Thr Gly Leu Pro Ala Leu Ile Ser
                20                  25

(2) INFORMATION FOR SEQ ID NO:5:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (xi) SEQUENCE DESCRIPTION: SEQ ID NO:5:

Lys Trp Lys Ser Phe Ile Lys Asn Leu Glu Lys Val Leu Lys Pro Gly
 1               5                  10                  15

Gly Leu Leu Ser Asn Ile Val Thr Ser Leu
                20                  25

(2) INFORMATION FOR SEQ ID NO:6:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (xi) SEQUENCE DESCRIPTION: SEQ ID NO:6:

Lys Trp Lys Ser Phe Ile Lys Asn Leu Glu Lys Val Leu Lys Lys Gly
 1               5                  10                  15

Pro Ile Leu Ala Asn Leu Val Ser Ile Val
                20                  25

(2) INFORMATION FOR SEQ ID NO:7:

(i) SEQUENCE CHARACTERISTICS:
            (A) LENGTH: 26 amino acids
            (B) TYPE: amino acid
            (D) TOPOLOGY: linear (ii) MOLECULE TYPE: peptide
```

```
    (xi) SEQUENCE DESCRIPTION: SEQ ID NO:7:

Lys Trp Lys Glu Phe Ile Lys Lys Leu Thr Thr Ala Val Lys Lys Val
  1               5                  10                  15

Leu Thr Thr Gly Leu Pro Ala Leu Ile Ser
             20                  25

(2) INFORMATION FOR SEQ ID NO:8:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:8:

Lys Trp Lys Lys Phe Ile Lys Glu Leu Gln Lys Val Leu Ala Pro Gly
  1               5                  10                  15

Gly Leu Leu Ser Asn Ile Val Thr Ser Leu
             20                  25

(2) INFORMATION FOR SEQ ID NO:9:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:9:

Lys Trp Lys Ser Phe Ile Lys Lys Leu Thr Ser Val Leu Lys Lys Val
  1               5                  10                  15

Val Thr Thr Ala Leu Pro Ala Leu Ile Ser
             20                  25

(2) INFORMATION FOR SEQ ID NO:10:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:10:

Lys Trp Lys Ser Phe Ile Lys Asn Leu Thr Lys Val Leu Lys Lys Val
  1               5                  10                  15

Val Thr Thr Ala Leu Pro Ala Leu Ile Ser
             20                  25

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:11:

Lys Trp Lys Leu Phe Lys Lys Gly Thr Gly Ala Val Leu Thr Val
  1               5                  10                  15

Leu Thr Thr Gly Leu Pro Ala Leu Ile Ser
             20                  25
```

(2) INFORMATION FOR SEQ ID NO:12:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:12:

```
Lys Trp Lys Ser Phe Ile Lys Lys Leu Thr Ser Val Leu Lys Lys Val
 1               5                  10                  15
Val Thr Thr Ala Lys Pro Leu Ile Ser Ser
                20                  25
```

(2) INFORMATION FOR SEQ ID NO:13:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:13:

```
Lys Lys Lys Ser Phe Ile Lys Leu Leu Thr Ser Ala Lys Val Ser Val
 1               5                  10                  15
Leu Thr Thr Ala Lys Pro Leu Ile Ser Ser
                20                  25
```

(2) INFORMATION FOR SEQ ID NO:14:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:14:

```
Lys Trp Lys Lys Phe Ile Lys Glu Leu Gln Lys Val Leu Lys Pro Gly
 1               5                  10                  15
Gly Leu Leu Ser Asn Ile Val Thr Ser Leu
                20                  25
```

(2) INFORMATION FOR SEQ ID NO:15:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:15:

```
Lys Lys Trp Arg Arg Val Leu Ser Gly Leu Lys Thr Gly Pro Ala
 1               5                  10                  15
Leu Ser Asn Val
            20
```

(2) INFORMATION FOR SEQ ID NO:16:

(i) SEQUENCE CHARACTERISTICS:
        (A) LENGTH: 20 amino acids
        (B) TYPE: amino acid -continued (D) TOPOLOGY: linear (ii) MOLECULE TYPE: peptide (xi) SEQUENCE DESCRIPTION: SEQ ID NO:16:

Lys Lys Trp Trp Arg Arg Val Leu Lys Gly Leu Ser Ser Gly Pro Ala
 1               5                  10                  15

Leu Ser Asn Val
            20

(2) INFORMATION FOR SEQ ID NO:17:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:17:

Lys Lys Trp Trp Arg Arg Ala Leu Gln Ala Leu Lys Asn Gly Pro Ala
 1               5                  10                  15

Leu Ser Asn Val
            20

(2) INFORMATION FOR SEQ ID NO:18:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:18:

Lys Lys Trp Trp Arg Arg Val Leu Ser Gly Leu Lys Thr Ala Gly Pro
 1               5                  10                  15

Ala Ile Gln Ser Val Leu Asn Lys
            20

(2) INFORMATION FOR SEQ ID NO:19:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:19:

Lys Lys Trp Trp Arg Arg Ala Leu Gln Gly Leu Lys Thr Ala Gly Pro
 1               5                  10                  15

Ala Ile Gln Ser Val Leu Asn Lys
            20

(2) INFORMATION FOR SEQ ID NO:20:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:20:

Lys Lys Trp Trp Lys Ala Gln Lys Ala Val Asn Ser Gly Pro Asn Ala

```
            1               5              10              15

Leu Gln Thr Leu Ala Gln
                20

(2) INFORMATION FOR SEQ ID NO:21:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:21:

Lys Lys Trp Trp Lys Ala Lys Lys Phe Ala Asn Ser Gly Pro Asn Ala
  1               5                  10                  15

Leu Gln Thr Leu Ala Gln
                20

(2) INFORMATION FOR SEQ ID NO:22:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:22:

Lys Lys Trp Trp Lys Phe Ile Lys Lys Ala Val Asn Ser Gly Thr Thr
  1               5                  10                  15

Gly Leu Gln Thr Leu Ala Ser
                20

(2) INFORMATION FOR SEQ ID NO:23:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:23:

Lys Lys Ser Phe Phe Lys Lys Leu Thr Ser Val Ala Ser Ser Val Leu
  1               5                  10                  15

Ser (2) INFORMATION FOR SEQ ID NO:24:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:24:

Trp Lys Val Phe Lys Ser Phe Ile Lys Lys Ala Ser Ser Phe Ala Gln
  1               5                  10                  15

Ser Val Leu Asp
            20

(2) INFORMATION FOR SEQ ID NO:25:
```

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:25:

Lys Lys Trp Arg Lys Ser Phe Phe Lys Gln Val Gly Ser Phe Asp Asn
 1               5                  10                  15

Ser Val (2) INFORMATION FOR SEQ ID NO:26:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (B) LOCATION: 4, 7, 8, 10, 11, 14 and 15
        (D) OTHER INFORMATION: where Xaa at positions 4, 7, 8, 10, 11,
            14 and 15 are selected from arginine, lysine, glutamic
            acid, aspartic acid, glutamine, asparagine, serine,
            histidine and threonine
        (B) LOCATION: 5, 6, 9, 12 and 13
        (D) OTHER INFORMATION: where Xaa at positions 5, 6, 9, 12 and
            13 are selected from isoleucine, valine, leucine,
            alanine, cysteine, glycine, phenylalanine, proline,
            tryptophan, tyrosine, norleucine and methionine (xi) SEQUENCE DESCRIPTION: SEQ ID NO:26:

Lys Trp Lys Xaa Xaa Xaa Xaa Xaa Xaa Xaa Xaa Xaa Xaa Xaa Xaa Val
 1               5                  10                  15

Leu Thr Thr Gly Leu Pro Ala Leu Ile Ser
             20                  25

(2) INFORMATION FOR SEQ ID NO:27:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (B) LOCATION: 4, 7, 8, 10, 11, 14 and 15
        (D) OTHER INFORMATION: where Xaa at positions 4, 7, 8, 10, 11,
            14 and 15 are selected from arginine, lysine, glutamic
            acid, aspartic acid, glutamine, asparagine, serine,
            histidine and threonine
        (B) LOCATION: 5, 6, 9, 12 and 13
        (D) OTHER INFORMATION: where Xaa at positions 5, 6, 9, 12 and
            13 are selected from isoleucine, valine, leucine,
            alanine, cysteine, glycine, phenylalanine, proline,
            tryptophan, tyrosine, norleucine and methionine (xi) SEQUENCE DESCRIPTION: SEQ ID NO:27:

Lys Trp Lys Xaa Xaa Xaa Xaa Xaa Xaa Xaa Xaa Xaa Xaa Xaa Xaa Val
 1               5                  10                  15

Val Thr Thr Ala Lys Pro Leu Ile Ser Ser
             20                  25

(2) INFORMATION FOR SEQ ID NO:28:

(i) SEQUENCE CHARACTERISTICS:
        (A) LENGTH: 26 amino acids

```
        (B) TYPE: amino acid
        (D) TOPOLOGY: linear (ii) MOLECULE TYPE: peptide (ix) FEATURE:
        (B) LOCATION: 4, 7, 8, 10, 11, 14 and 15
        (D) OTHER INFORMATION: where Xaa at positions 4, 7, 8, 10, 11,
            14 and 15 are selected from arginine, lysine, glutamic
            acid, aspartic acid, glutamine, asparagine, serine,
            histidine and threonine
        (B) LOCATION: 5, 6, 9, 12 and 13
        (D) OTHER INFORMATION: where Xaa at positions 5, 6, 9, 12 and
            13 are selected from isoleucine, valine, leucine,
            alanine, cysteine, glycine, phenylalanine, proline,
            tryptophan, tyrosine, norleucine and methionine (xi) SEQUENCE DESCRIPTION: SEQ ID NO:28:

Lys Trp Lys Xaa Xaa Xaa Xaa Xaa Xaa Xaa Xaa Xaa Xaa Xaa Xaa Ile
 1               5                  10                  15

Leu Thr Thr Gly Leu Pro Ala Leu Ile Ser
            20                  25

(2) INFORMATION FOR SEQ ID NO:29:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (B) LOCATION: 4, 7, 8, 10, 11, 14 and 15
        (D) OTHER INFORMATION: where Xaa at positions 4, 7, 8, 10, 11,
            14 and 15 are selected from arginine, lysine, glutamic
            acid, aspartic acid, glutamine, asparagine, serine,
            histidine and threonine
        (B) LOCATION: 5, 6, 9, 12 and 13
        (D) OTHER INFORMATION: where Xaa at positions 5, 6, 9, 12 and
            13 are selected from isoleucine, valine, leucine,
            alanine, cysteine, glycine, phenylalanine, proline,
            tryptophan, tyrosine, norleucine and methionine (xi) SEQUENCE DESCRIPTION: SEQ ID NO:29:

Lys Trp Lys Xaa Xaa Xaa Xaa Xaa Xaa Xaa Xaa Xaa Xaa Xaa Xaa Gly
 1               5                  10                  15

Gly Leu Leu Ser Asn Ile Val Thr Ser Leu
            20                  25

(2) INFORMATION FOR SEQ ID NO:30:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (B) LOCATION: 4, 7, 8, 10, 11, 14 and 15
        (D) OTHER INFORMATION: where Xaa at positions 4, 7, 8, 10, 11,
            14 and 15 are selected from arginine, lysine, glutamic
            acid, aspartic acid, glutamine, asparagine, serine,
            histidine and threonine
        (B) LOCATION: 5, 6, 9, 12 and 13
        (D) OTHER INFORMATION: where Xaa at positions 5, 6, 9, 12 and
            13 are selected from isoleucine, valine, leucine,
            alanine, cysteine, glycine, phenylalanine, proline,
            tryptophan, tyrosine, norleucine and methionine (xi) SEQUENCE DESCRIPTION: SEQ ID NO:30:
```

```
Lys Trp Lys Xaa Xaa Xaa Xaa Xaa Xaa Xaa Xaa Xaa Xaa Xaa Xaa Gly
 1               5                  10                  15

Pro Ile Leu Ala Asn Leu Val Ser Ile Val
                20                  25
```

(2) INFORMATION FOR SEQ ID NO:31:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (B) LOCATION: 7, 8, 10 and 11
        (D) OTHER INFORMATION: where Xaa at positions 7, 8, 10 and 11
            are selected from isoleucine, valine, leucine, alanine,
            cysteine, glycine, phenylalanine, proline, tryptophan,
            tyrosine, norleucine and methionine
        (B) LOCATION: 9, 12, and 13
        (D) OTHER INFORMATION: where Xaa at positions 9, 12, and 13
            are selected from arginine, lysine, glutamic acid,
            aspartic acid, glutamine, asparagine, serine, histidine
            and threonine (xi) SEQUENCE DESCRIPTION: SEQ ID NO:31:

```
Lys Lys Trp Trp Arg Arg Xaa Xaa Xaa Xaa Xaa Xaa Xaa Gly Pro Ala
 1               5                  10                  15

Leu Ser Asn Val
            20
```

(2) INFORMATION FOR SEQ ID NO:32:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (B) LOCATION: 7...7
        (D) OTHER INFORMATION: where Xaa at position 7 is from about
           14-24 amino acid residues selected from isoleucine,
           valine, leucine, alanine, cysteine, glycine,
           phenylalanine, proline, tryptophan, tyrosine, norleucine,
           methionine, arginine, lysine, glutamic acid, aspartic
           acid, glutamine, asparagine, serine, histidine and
           threonine (xi) SEQUENCE DESCRIPTION: SEQ ID NO:32:

```
Lys Lys Trp Trp Arg Arg Xaa
 1               5
```

(2) INFORMATION FOR SEQ ID NO:33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: 6...6
        (D) OTHER INFORMATION: where Xaa at position 6 is from about
           14-24 amino acid residues selected from isoleucine,
           valine, leucine, alanine, cysteine, glycine,
           phenylalanine, proline, tryptophan, tyrosine, norleucine,
           methionine, arginine, lysine, glutamic acid, aspartic
           acid, glutamine, asparagine, serine, histidine and threonine (xi) SEQUENCE DESCRIPTION: SEQ ID NO:33:

Lys Lys Trp Trp Lys Xaa
 1               5

(2) INFORMATION FOR SEQ ID NO:34:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:34:

Lys Trp Lys Ser Phe Ile Lys Lys
 1               5

(2) INFORMATION FOR SEQ ID NO:35:

(i) SEQUENCE CHARACTERISTICS:
      (A) LENGTH: 24 amino acids
      (B) TYPE: amino acid
      (D) TOPOLOGY: linear (ii) MOLECULE TYPE: peptide (ix) FEATURE:
      (B) LOCATION: 6
      (D) OTHER INFORMATION: where Xaa at position 6 is selected
          from arginine, lysine, glutamic acid, aspartic acid,
          glutamine, asparagine, serine, histidine and threonine
      (B) LOCATION: 4 and 5
      (D) OTHER INFORMATION: where Xaa at positions 4 and 5 are
          selected from isoleucine, valine, leucine, alanine,
          cysteine, glycine, phenylalanine, proline, tryptophan,
          tyrosine, norleucine and methionine (xi) SEQUENCE DESCRIPTION: SEQ ID NO:35:

Lys Lys Trp Trp Arg Arg Xaa Xaa Xaa Gly Leu Lys Thr Ala Gly Pro
 1               5                  10                  15

Ala Ile Gln Ser Val Leu Asn Lys
                20

(2) INFORMATION FOR SEQ ID NO:36:

(i) SEQUENCE CHARACTERISTICS:
      (A) LENGTH: 26 amino acids
      (B) TYPE: amino acid
      (D) TOPOLOGY: linear (ii) MOLECULE TYPE: peptide (xi) SEQUENCE DESCRIPTION: SEQ ID NO:36:

Lys Trp Lys Leu Phe Lys Lys Ile Gly Ile Gly Ala Val Leu Lys Val
 1               5                  10                  15

Leu Thr Thr Gly Leu Pro Ala Leu Ile Ser
                20                  25

(2) INFORMATION FOR SEQ ID NO:37:

(i) SEQUENCE CHARACTERISTICS:
      (A) LENGTH: 28 amino acids (B) TYPE: amino acid
            (D) TOPOLOGY: linear (ii) MOLECULE TYPE: peptide (xi) SEQUENCE DESCRIPTION: SEQ ID NO:37:

Lys Trp Lys Leu Phe Lys Lys Ile Gly Ile Gly Ala Val Leu Lys Val
 1               5                  10                  15

Leu Thr Thr Gly Leu Pro Ala Leu Lys Lys Thr Lys
                20                  25

(2) INFORMATION FOR SEQ ID NO:38:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (B) LOCATION: 7, 9, 10, 12, 13, 14, 18, 19, 21, 23, 24, 25.
        (D) OTHER INFORMATION: where Xaa at position 7 is selected
            from valine and alanine; Xaa at position 9 is selected
            from serine, lysine and glutamine; Xaa at position 10 is
            selected from glycine and alanine; Xaa at position 12 is
            selected from lysine and serine; Xaa at position 13 is
            selected from threonine, serine and asparagine; Xaa at
            position 14 is selected from alanine or absent; Xaa at
            position 18 is selected from isoleucine and leucine; Xaa
            at position 19 is selected from glutamine or absent; Xaa
            at position 21 is selected from asparagine or absent; Xaa
            at position 23 is selected from leucine or absent; Xaa at
            position 24 is selected from asparagine or absent; Xaa at
            position 25 is selected from lysine or absent.

(xi) SEQUENCE DESCRIPTION: SEQ ID NO:38:

Lys Lys Trp Trp Arg Arg Xaa Leu Xaa Xaa Leu Xaa Xaa Xaa Gly Pro
 1               5                  10                  15

Ala Xaa Xaa Ser Xaa Val Xaa Xaa Xaa
                20                  25

(2) INFORMATION FOR SEQ ID NO:39:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (B) LOCATION: 6, 7, 8, 10, 11, 15, 16, 17, 23.
        (D) OTHER INFORMATION: where Xaa at position 6 is selected
            from phenylalanine or absent; Xaa at position 7 is
            selected from alanine and isoleucine; Xaa at position 8
            is selected from glutamine and lysine; Xaa at position
            10 is selected from alanine and phenylalanine; Xaa at
            position 11 is selected from valine and alanine; Xaa at
            position 15 is selected from proline and threonine; Xaa
            at position 16 is selected from asparagine and threonine;
            Xaa at position 17 is selected from alanine and glycine;
            Xaa at position 23 is selected from glutamine and serine.

(xi) SEQUENCE DESCRIPTION: SEQ ID NO:39:

Lys Lys Trp Trp Lys Xaa Xaa Xaa Lys Xaa Xaa Asn Ser Gly Xaa Xaa
 1               5                  10                  15

Xaa Leu Gln Thr Leu Ala Xaa
                20